US012661347B2

(12) United States Patent
Greinwald et al.

(10) Patent No.: US 12,661,347 B2

(45) Date of Patent: Jun. 23, 2026

(54) SYSTEMIC FORMULATION OF A PYRIDINONE DERIVATE FOR COELIAC DISEASE

(71) Applicant: Dr. Falk Pharma GmbH, Freiburg (DE)

(72) Inventors: Roland Greinwald, Kenzingen (DE); Wolfgang Mohr, Freiburg (DE); Bernhard Tewes, Vorstetten (DE); Rudolf Wilhelm, Bischweier (DE); Ralf Mohrbacher, Freiburg (DE)

(73) Assignee: Dr. Falk Pharma GmbH, Freiburg (DE)

( * ) Notice: Subject to any disclaimer, the term of this patent is extended or adjusted under 35 U.S.C. 154(b) by 661 days.

(21) Appl. No.: 17/996,770

(22) PCT Filed: Apr. 24, 2021

(86) PCT No.: PCT/EP2021/060763

§ 371 (c)(1), (2) Date: Oct. 20, 2022

(87) PCT Pub. No.: WO2021/214337

PCT Pub. Date: Oct. 28, 2021

(65) Prior Publication Data

US 2023/0165844 A1 Jun. 1, 2023

(30) Foreign Application Priority Data

Apr. 24, 2020 (EP) .................................... 20171440
Dec. 3, 2020 (EP) .................................... 20211713

(51) Int. Cl.
*A61K 31/4439* (2006.01)
*A61K 9/20* (2006.01)
*A61K 9/48* (2006.01)

(52) U.S. Cl.
CPC ........ *A61K 31/4439* (2013.01); *A61K 9/2054* (2013.01); *A61K 9/4825* (2013.01); *A61K 9/4858* (2013.01); *A61K 9/4866* (2013.01)

(58) Field of Classification Search
CPC . A61K 31/4439; A61K 9/2054; C07D 401/12
See application file for complete search history.

(56) References Cited

U.S. PATENT DOCUMENTS 9,434,763 B2 * 9/2016 Buchold .................. A61P 7/02
2011/0229568 A1 9/2011 Oertel
(Continued)

FOREIGN PATENT DOCUMENTS

CN 104603109 A 5/2015
EP 2687511 1/2014
(Continued)

OTHER PUBLICATIONS

Handbook of Pharmaceutical Excipients, 6th Ed, 2009, pp. 11-12 and 317-324 (Year: 2009).*
(Continued)

*Primary Examiner* — San Ming R Hui
(74) *Attorney, Agent, or Firm* — Sterne, Kessler, Goldstein & Fox P.L.L.C.

(57) ABSTRACT

The present invention relates to a systemic formulation, in particular an oral formulation, for the prophylaxis and/or treatment of coeliac disease, i.e. for use in the prophylaxis and/or treatment of coeliac disease.

24 Claims, 9 Drawing Sheets

| Dose | 10 mg | 20 mg | 50 mg | 100 mg |
|---|---|---|---|---|
| $C_{max}$ [ng/mL] | 59.8±19.2 | 127±45.4 | 375±229 | 840±349 |
| $AUC_{0-t}$ [ng/mL*h] | 205±50.3 | 442±159 | 1106±694 | 2211±821 |
| $t_{max}$ [h], Median<br>Range | 1.00<br>0.750-2.00 | 1.25<br>0.750-2.00 | 1.00<br>0.500-2.00 | 1.13<br>0.750-2.00 |

(56) References Cited

U.S. PATENT DOCUMENTS

| | | | |
|---|---|---|---|
| 2015/0203535 | A1 | 7/2015 | Buchold et al. |
| 2023/0165845 | A1 | 6/2023 | Greinwald et al. |

FOREIGN PATENT DOCUMENTS

| | | | |
|---|---|---|---|
| EP | 3210599 | A1 | 8/2017 |
| JP | 2003252797 | A | 9/2003 |
| JP | 2011529445 | A | 12/2011 |
| JP | 2015529645 | A | 10/2015 |
| JP | 2017502062 | A | 1/2017 |
| JP | 2018519279 | A | 7/2018 |
| JP | 2019001787 | A | 1/2019 |
| WO | WO-2011102504 | A1 | 8/2011 |
| WO | WO-2018122419 | A1 | 7/2018 |
| WO | WO 2019/202052 | | 10/2019 |
| WO | WO-2020027011 | A1 | 2/2020 |
| WO | WO-2021/214338 | A1 | 10/2021 |
| WO | WO-2023072878 | A1 | 5/2023 |

OTHER PUBLICATIONS

Peterson, B., et al., “Drug Bioavailability Enhancing Agents of Natural Origin (Bioenhancers) that Modulate Drug Membrane Permeation and Pre-Systemic Metabolism,” Pharmaceutics 11(33):1-46, MDPI, Switzerland (2019).

Warren, D. B., et al., “Using Polymeric Precipitation Inhibitors to Improve the Absorption of Poorly Water-Soluble Drugs: A Mechanistic Basis for Utility,” Journal of Drug Targeting 18(10):704-731, Informa UK, Ltd., United Kingdom (2010).

International Search Report and Written Opinion mailed Jul. 1, 2021 in PCT Application No. PCT/EP2021/060763, filed Apr. 24, 2021.

International Search Report and Written Opinion mailed Jul. 2, 2021 in PCT Application No. PCT/EP2021/060764, filed Apr. 24, 2021, European Patent Office, the Netherlands, 9 pages.

Luciani, A., et al., “Defective CFTR induces aggresome formation and lung inflammation in cystic fibrosis through ROS-mediated autophagy inhibition,” Nature Cell Biology 12:863-875, Macmillan Publishers Limited, United States (2010).

Huang, F., et al., “Particulate Matter and Hospital Admissions for Stroke in Beijing, China: Modification Effects by Ambient Temperature,” Journal of the American Heart Association 5:e003437, American Heart Association, United States (2016).

Olsen, K. C., et al., “Inhibition of Transglutaminase 2, a Novel Target for Pulmonary Fibrosis, by Two Small Electrophilic Molecules,” American Journal of Respiratory Cell and Molecular Biology 50(4):737-747, American Thoracic Society, United States (2014).

Korpimäki, S., et al. “Gluten-sensitive hypertransaminasemia in celiac disease: an infrequent and often subclinical finding,” The American Journal of Gastroenterology 106:1689-1696, The American College of Gastroenterology, United States (2011).

Kahaly, G. J., et al., “Celiac disease and endocrine autoimmunity—the genetic link,” Autoimmun. Rev. 17:1169-1175, Elsevier, Netherlands (2018).

Lebwohl, B., et al., “Celiac disease,” Lancet 391:70-81, Elsevier, Netherlands (2018).

Ludvigsson, J. F., et al., “The Oslo definitions for coeliac disease and related terms,” Gut 62:43-52, British Medical Association, United Kingdom (2012).

Schuppan, D., et al., “Celiac disease: from pathogenesis to novel therapies,” Gastroenterology 137(6):1912-1933, Elsevier, Netherlands (2009).

Lauzier, A., et al., “Transglutaminase 2 Cross-linking Activity is Linked to Invadopodia Formation and Cartilage Breakdown in Arthritis,” Arthritis Research & Therapy 14:R159, BioMed Central, United Kingdom (2012).

Sanchez-Lara, A. C., et al., “Feline Chronic Kidney Disease is Associated with Upregulation of Transglutaminase 2: A Collagen Cross-Linking Enzyme,” Veterinary Pathology 52(3):513-523, Sage Publications, United States (2015).

Leffler, D. A., et al., “A validated disease-specific symptom index for adults with celiac disease,” Clin. Gastroenterol. Hepatol. 7(12):1328-1334, Elsevier, Netherlands (2009).

Häuser et al., “Development and validation of the Celiac Disease Questionnaire (CDQ), a disease-specific health-related quality of life measure for adult patients with celiac disease,” J. Clin. Gastroenterol. 41:157-166, Lippincott Williams & Wilkins, United States (2007).

Huang, L., et al., “Transglutaminase inhibition ameliorates experimental diabetic nephropathy” Kidney International 76(4):383-394, Elsevier, Netherlands (2009).

Daneshpour, N., et al., “Targeted Delivery of a Novel Group of Site-Directed Transglutaminase Inhibitors to the Liver using Liposomes: A New Approach for the Potential Treatment of Liver Fibrosis,” Journal of Drug Targeting 19(8):624-631, Informa UK, Ltd., United Kingdom (Sep. 2010).

Ventura, M.A.E., et al., “Sul161—The Oral Transglutaminase 2 (TG2) Inhibitor Zed1227 Blocks TG2 Activity in a Mouse Model of Intestinal Inflammation,” Gastroenterology 154(6):S-490, American Gastroenterological Association, United States (May 2018).

Office Action mailed Jul. 2, 2025, in U.S. Appl. No. 17/996,775, inventors Greinwald, R., et al., § 371(c) Date: Oct. 20, 2022, 18 pages.

Huang, Y., et al., “Fundamental Aspects of Solid Dispersion Technology for Poorly Soluble Drugs,” Acta Pharmaceutica Sinica B 4(1):18-25 (Dec. 2023).

Leuner, C., et al., “Improving Drug Solubility for Oral Delivery Using Solid Dispersions,” European Journal of Pharmaceutics and Biopharmaceutics, 50(1):47-60 (Jul. 2000).

Grenard, P., et al., “Transglutaminase-Mediated Cross-Linking is Involved in the Stabilization of Extracellular Matrix in Human Liver Fibrosis,” Journal of Hepatology 35(3):367-375, Elsevier, Netherlands (Sep. 2001).

Mirza, A., et al., “A Role for Tissue Transglutaminase in Hepatic Injury and Fibrogenesis, and its Regulation by NF-kappaB,” American Journal of Physiology 272(2 Pt 1):G281-288, American Physiological Society, United States (Feb. 1997).

* cited by examiner

| Dose | 10 mg | 20 mg | 50 mg | 100 mg |
|---|---|---|---|---|
| $C_{max}$ [ng/mL] | 59.8±19.2 | 127±45.4 | 375±229 | 840±349 |
| $AUC_{0-t}$ [ng/mL*h] | 205±50.3 | 442±159 | 1106±694 | 2211±821 |
| $t_{max}$ [h], Median | 1.00 | 1.25 | 1.00 | 1.13 |
| Range | 0.750-2.00 | 0.750-2.00 | 0.500-2.00 | 0.750-2.00 |

| Clinical PK data (CEC-2/BIO) | | $C_{max}$ / $IC_{(10-90)}$ | | |
|---|---|---|---|---|
| Drug level | $C_{max}$ ( ≡ drug conc. at target site) | $IC_{10}$ (8.5 ng/mL) | $IC_{50}$ (54.3 ng/mL) | $IC_{90}$ (208.1 ng/mL) |
| 10 mg | 59.8 ng/mL | 7.0 | 1.1 | 0.3 |
| 20 mg | 127.0 ng/mL | 14.9 | 2.3 | 0.6 |
| 50 mg | 375.0 ng/mL | 44.1 | 6.9 | 1.8 |
| 100 mg | 840.0 ng/mL | 98.8 | 15.5 | 4.0 |

Individual patient's villous height-to-crypt depth ratio (VH:CrD)

Individual patient's intraepithelial lymphocyte (IEL) density

Celiac Disease Questionaire Score (Change from Baseline)

A.

B.

SYSTEMIC FORMULATION OF A PYRIDINONE DERIVATE FOR COELIAC DISEASE

The present application is the national phase entry of PCT Application No. PCT/EP2021/060763, filed Apr. 24, 2021, which claims priority to EP application Nos. 20171440.9, filed Apr. 24, 2020, and 20211713.1, filed Dec. 3, 2020, each of which are incorporated by reference in their entireties.

The present invention relates to a systemic formulation in particular an oral formulation for the prophylaxis and/or treatment of coeliac disease, i.e. for use in the prophylaxis and/or treatment of coeliac disease.

BACKGROUND OF THE INVENTION

Coeliac disease, a gluten intolerance, is an indication with high prevalence. Coeliac disease is characterized by a chronic inflammation of the mucosa of the small intestine. In patients concerned, the small intestinal epithelium is successively destroyed after ingestion of gluten-containing food resulting in reduced absorption of nutrients which again has a large impact on the patients concerned and is for example associated with symptoms such as loss of weight, anemia, diarrhea, nausea, loss of appetite and fatigue. Due to these findings, there is a large demand for the development of a medicinal product for the treatment of coeliac disease as well as of other diseases associated with tissue transglutaminase. The tissue transglutaminase is a central element during pathogenesis of celiac disease. The endogenous enzyme catalyses the deamidation of gluten/gliadine in the small intestinal mucosa and thus highly increases the inflammatory reaction. Therefore, inhibitors of the tissue transglutaminase are suitable to be used as active agents for coeliac disease. Although there are some compounds available, which might be suitable for the treatment of coeliac disease, several drawbacks are associated with these compounds in particular the selectivity. Moreover, it is still a great problem in the pharmaceutical field to establish an appropriate bioavailability of a drug under physiological conditions in particular in case of a systemic therapy. Further, in case of the coeliac disease topical availability in the duodenum as well as a high drug level in the tissue of the duodenum have to be achieved.

It is the objective of the present invention to provide a pharmaceutical formulation especially useful for the prophylaxis and/or treatment of coeliac disease exhibiting a topical availability, bioavailability, and an inhibitory effect in vivo.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The objective of the present invention is solved by a formulation preferably a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

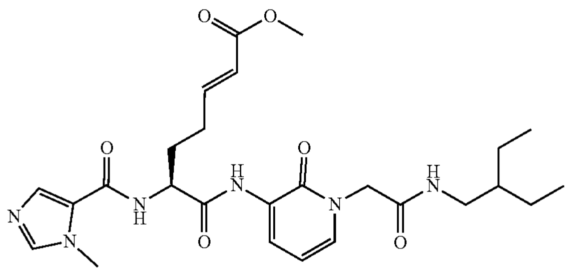

, or an enantiomer, a solvate, a hydrate or a pharmaceutically acceptable salt of formula (I) for use in the prophylaxis and/or treatment of coeliac disease.

Unexpectedly, it could be found that the compound according to formula (I) exhibits a topical availability in the duodenum and systemic availability (bioavailability) in the tissue of the duodenum in case of oral administration. Pharmacokinetic studies demonstrated bioavailability after oral administration in various species which was largely increased in human by application of the systemic formulation (example 3 and 4)

DESCRIPTION OF THE INVENTION

The term "systemic formulation" refers to a pharmaceutical composition suitable for administration such that a drug or active agent is systemically available throughout the body of an organism, e.g. a form of medication for the circulatory system so that the entire body is affected. Administration can take place via enteral administration (absorption of the drug through the gastrointestinal tract) or parenteral administration (e.g. pulmonary, nasal, injection or infusion). Preferably, the term "systemic formulation" excludes formulation for an intravenous application. The circulatory system, also called the cardiovascular system or the vascular system, is an organ system that permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis.

The circulatory system includes the lymphatic system, which circulates lymph. The passage of lymph for example takes much longer than that of blood. Thus, the term "systemic formulation" refers to a formulation, wherein the drug is distributed throughout the body of an organism by e.g. the blood or lymphatic system throughout the body, for example, after an intravenous or intramuscular injection or taking a tablet, i.e. after an enteral, in particular an oral or a parenteral administration.

The systemic formulations as disclosed herein are preferably in the form of a tablet, coated tablet, capsule, powder, or granules.

In contrast thereto, a "topical formulation" is a formulation that is applied to a particular place on or in the body where it should act. Topical means "place", "locally", at a specific site", "externally" or "limited to a specific site of the body". Thus, the risk of possible unwanted side effects in other areas of the organism can be reduced. Most often topical administration means application to body surfaces such as the skin or mucous membranes to treat ailments via a large range of classes including creams, foams, gels, lotions, and ointments. Many topical medications are epicutaneous, meaning that they are applied directly to the skin. Topical medications may also be inhalational, such as asthma medications, or applied to the surface of tissues other than the skin, such as eye drops applied to the conjunctiva, or ear drops placed in the ear, medications applied to the surface of a tooth or application of the drug by means of a pump such as an osmotic pump.

The topical formulations include aural, buccal, endobronchial, epicutaneous, inhalation, intraarticular, into the gluteus maximus muscle, intracardiac, intracutaneous, intralumbar, intralymphatic, intramammarial, intranasal, intraneuronal, intraocular, intraorbital, intraosseous, intrapericadial, intrapulmonary, intrathecal, intratracheal, intraurethral, intrauterine, intraventricular, intravesical, intravitreal, conjunctival, cutan, nasal, perineural, retrobulbar, subconjunctival, vaginal, and ciliary.

The term "parenteral formulation", as used herein refers, to a formulation, which usually is administered by injection or infusion, and includes, without limitation, epidural, intraarterial, intravenous, intravasal, intravascular, intramuscular, intraperitoneal, intrapleural, subcutaneous, subcuticular, and transdermal injection and infusion. Preferably, a parenteral formulation is selected from the group comprising or consisting of epidural, intravasal, intravascular, intramuscular, intraperitoneal, intrapleural, subcutaneous, subcuticular, and transdermal injection and infusion. Preferably, the intraarterial and intravenous formulations are excluded from the parenteral formulations.

"Enteral formulation", as used herein, refers to a formulation being usually a medication which is absorbed through the mouth (per os, orally, perorally): tablets, dragees, capsules, juices, drops, etc. These medicines are absorbed into the blood in the gastrointestinal tract, and then enter the liver via the portal vein system and then into the bloodstream via the hepatic vein. The term, as used herein, refers to a formulation which is usually administered including, without limitation enteral, intragastral, sublingual, peroral (oral), and rectal. Preferably, enteral formulation consists of a formulation selected from the group comprising or consisting of enteral, intragastral, sublingual, peroral (oral), and rectal.

"Oral formulation", as used herein, refers to a formulation being a medication which is absorbed through the mouth (per os, orally, perorally): tablets, dragees, capsules, juices, drops, etc. These medicines are absorbed into the blood in the gastrointestinal tract, and then enter the liver via the portal vein system and then into the bloodstream via the hepatic vein. The term, as used herein, refers to a formulation which is administered orally.

The systemic formulation can be in a liquid or solid form including solutions, oral drops, suspensions, emulsions, powders, granules such as effervescent granules, tablets such as uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules, powders, granules, micro granules, and pellets. In particular, the systemic formulation can be a liquid preparation including oral solutions, suspensions, emulsions, powders and granules for oral solutions and suspensions, oral drops, powder for oral drops, syrups and powder and granules for syrups or in a solid form including uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules. Uncoated and coated tablets, and capsules, either hard or soft are the preferred pharmaceutical formulations. Most preferably, the formulation is a tablet or a capsule. As an example, there may be mentioned water or water/propylene glycol solutions for parenteral injections or addition of sweeteners and opacifiers for oral solutions, suspensions, and emulsions. Preferably, the systemic formulation is a solid formulation, more preferably a solid enteral formulation, and most preferably an oral formulation or a solid oral formulation.

"Topical administration", as used herein, refers to the administration of a topical formulation.

"Systemic administration", as used herein, refers to the administration of a systemic formulation.

"Topical availability", as used herein, refers to the release of the drug from its formulation such as from a vehicle of a formulation or from a tablet to the place at which the drug should be absorbed by the specific tissue or organ so that the drug could act at all.

"Systemic availability", as used herein, refers to the proportion of the dose of a drug that reaches the systemic circulation intact after administration by a route other than intravenous. The term "systemic availability" also refers to the extent to which a drug or other substance is taken up by a specific tissue or organ after administration. For example, a drug which is orally administered and overcomes the epithelial barrier of the intestine is in the tissue of the intestine, and thus it has a systemic availability or in the other words it is systemically available. "Systemic availability" and "systemic available" are synonymous for "bioavailability" or "bioavailable". Thus, also topically administered compounds can exhibit a systemic availability, which is of particular importance when the pharmaceutical target is located beyond the epithelial barrier as it is in coeliac disease.

The term "drug level" refers to the level of the drug in the plasma, tissue or organ, and the phrase "systemic availability at the target site" refers to the same aspect.

As used herein, the term "pharmaceutically acceptable salts" refers to salts of certain ingredient(s) which possess the same activity as the unmodified compound(s) and which are neither biologically nor otherwise undesirable.

A pharmaceutically acceptable salt can be formed with, for example, organic or inorganic acids. Suitable acids include acetic acid, acetylsalicylic acid, organic di-carboxylic acid such as oxalic acid, malonic acid, succinic acid, glutaric acid, tartaric acid, fumaric acid, maleic acid, malic acid, adipic acid, organic tri-carboxylic acid such as citric acid, or sodium hydrogen citrate alginic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids. Preferably, the acid is adipic acid, fumaric acid, glutaric acid, more preferably, the acid is adipic acid.

Thus, a further aspect of the present invention is directed to the salt of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

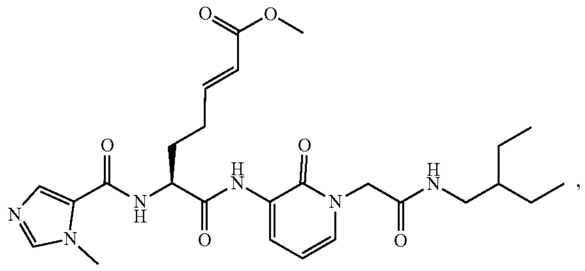

or an enantiomer, a solvate or a hydrate thereof for use in the prophylaxis and/or treatment of coeliac disease.

An embodiment of the invention is related to a systemic formulation containing a salt of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

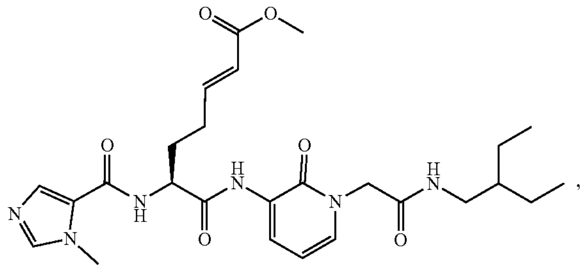

and adipic acid, or an enantiomer, a solvate or a hydrate of the salt of formula (I) and adipic acid for use in the prophylaxis and/or treatment of coeliac disease.

As used herein, the term "solvates" refers to those forms of a compound in particular the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate which form a complex through coordination with solvent molecules.

As used herein, the term "hydrates" refers to those forms of a compound in particular the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate which form a complex through coordination with water molecules.

As used herein, the term "effective amount" or "therapeutically effective amount" of an active agent, or a pharmaceutically active agent or drug or an active pharmaceutical ingredient, which are synonymous herein, refers to an amount of an active agent or pharmaceutically active agent or a drug or active pharmaceutical ingredient sufficient enough to have the desired pharmacological effect. Accordingly, these amounts are efficient to treat the disease but low enough to avoid serious side effects. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

As used herein, the terms "active agent", "pharmaceutically active agent", "drug" or "active pharmaceutical ingredient", which are synonymously used herein, refer to a compound exhibiting a therapeutic effect upon a mammal in particular a human.

As used herein, the term "pharmaceutical composition" refers to a composition which, upon administration, demonstrates a therapeutic effect upon a mammal.

Systemic formulations for use in the prophylaxis and/or treatment of coeliac disease according to the invention as described herein, preferably contains (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

An embodiment of the present invention is thus direct to a systemic formulation for use in the prophylaxis and/or treatment of coeliac disease containing (5, E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I) for use in the prophylaxis and/or treatment of coeliac disease:

(I)

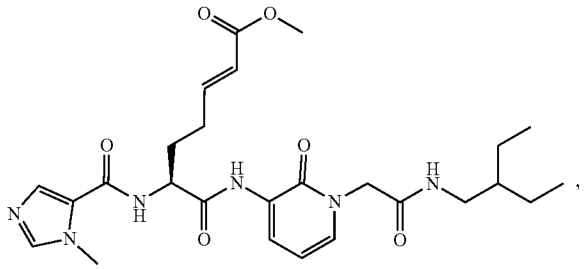

Further, the systemic formulation can be an enteral or parenteral formulation. An embodiment according to the invention is therefore related to a systemic formulation for use in the prophylaxis and/or treatment of coeliac disease containing (5, E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is in form of an enteral or parenteral formulation.

It is preferred if the systemic formulation is in form of an oral formulation, in particular an oral solid formulation. An oral formulation is a specific form of an enteral formulation. Therefore, a preferred embodiment of the invention is directed to a systemic formulation for use in the prophylaxis and/or treatment of coeliac disease containing (5, E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is in form of an oral formulation.

Furthermore, (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate can be administered in form of its pharmaceutically active salts, solvate or hydrate, optionally using essentially non-toxic pharmaceutically acceptable carriers, matrix, excipients or extenders. Formulations are prepared in a known manner in a conventional solid or fluid carrier using conventional pharmaceutically acceptable excipient in a suitable dose.

Thus, the systemic formulation according to the invention can further comprise an excipient. An embodiment according to the invention is thus directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient.

For duodenal-targeting, i.e. duodenum specific drug delivery, a formulation showing fast release after stomach passage is necessary. After that, the administered drug dose has to dissolve quickly and completely. The pH variations in the stomach after the oral administration have to be compensated and it should be ensured that the administered drug dose is efficiently dissolved. The larger the systemic availability (AUC) in conjunction with the mucosal uptake in the duodenum (indicated by an early tmax), the higher pharmacological effect to be expected.

The release in the duodenum is indicated by an early tmax, wherein tmax is the time at which the maximal concentration in the plasma, tissue or organ can be measured.

The excipient can be an acidifier. The term "acidifier" refers to a substance which, when dissolved in water, produces a pH level of less than 7.0. Thus, systemic formulation according to the invention can comprise an acidifier. Acidifiers include organic acids such as ascorbic acid, organic di-carboxylic acid such as oxalic acid, malonic acid, succinic acid, glutaric acid, tartaric acid, fumaric acid, maleic acid, malic acid, adipic acid (hexanedioic acid), or glutamic acid, and organic tri-carboxylic acid such as citric acid, or sodium hydrogen citrate. Preferably, the acidifier is adipic acid.

Preferred "acidifiers" for the systemic formulations as disclosed herein are selected from the group consisting of ascorbic acid, organic di-carboxylic acids such as oxalic acid, malonic acid, succinic acid, glutaric acid, tartaric acid, fumaric acid, maleic acid, malic acid, adipic acid, glutamic acid, and organic tri-carboxylic acids, citric acid, and sodium hydrogen citrate.

More preferred "acidifiers" for the systemic formulations as disclosed herein are selected from the group consisting of adipic acid, fumaric acid, and glutaric acid.

Thus, the systemic formulation according to the invention can comprise an acidifier.

A preferred embodiment according to the invention is related to a systemic formulation preferably for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier.

Another preferred embodiment according to the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I)

(I)

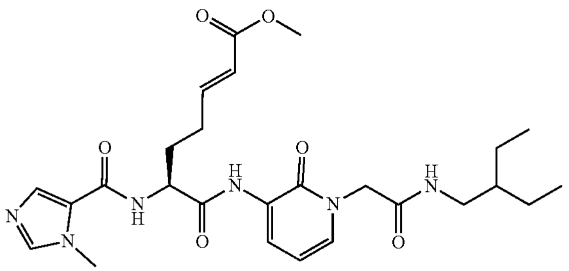

, or an enantiomer, a solvate, a hydrate or a pharmaceutically acceptable salt thereof, and at least one acidifier.

A preferred embodiment according to the invention is related to a systemic formulation preferably for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier, and wherein at least one acidifier is selected from the group comprising or consisting of organic di-carboxylic acid and organic tri-carboxylic acid. Preferably, at least one acidifier is selected from the group consisting of organic di-carboxylic acid and organic tri-carboxylic acid. More preferably, the at least one acidifier is selected from the group the group comprising or consisting of organic di-carboxylic acid and organic tri-carboxylic acid. Even more preferably, the at least one acidifier is selected from the group the group consisting of organic di-carboxylic acid and organic tri-carboxylic acid.

Thus, a preferred embodiment according to the invention is related to a systemic formulation preferably for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is selected from the group comprising or consisting of organic di-carboxylic acid and organic tri-carboxylic acid.

A preferred embodiment according to the invention is related to a systemic formulation preferably for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier, and wherein at least one acidifier is selected from the group comprising or consisting of ascorbic acid, organic di-carboxylic acids such as oxalic acid, malonic acid, succinic acid, glutaric acid, tartaric acid, fumaric acid, maleic acid, malic acid, adipic acid, glutamic acid, and organic tri-carboxylic acids, citric acid, and sodium hydrogen citrate. Preferably, at least one acidifier is selected from the group consisting of ascorbic acid, oxalic acid, malonic acid, succinic acid, glutaric acid, tartaric acid, fumaric acid, maleic acid, malic acid, adipic acid, glutamic acid, citric acid, and sodium hydrogen citrate. More preferably, the at least one acidifier is selected from the group comprising or consisting of oxalic acid, malonic acid, succinic acid, glutaric acid, tartaric acid, fumaric acid, maleic acid, malic acid, adipic acid (hexanedioic acid), or glutamic acid.

A preferred embodiment according to the invention is related to a systemic formulation preferably for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is selected from the group comprising or consisting of oxalic acid, malonic acid, succinic acid, glutaric acid, tartaric acid, fumaric acid, maleic acid, malic acid, adipic acid (hexanedioic acid), or glutamic acid.

A preferred embodiment according to the invention is related to a systemic formulation preferably for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is selected from the group comprising or consisting of adipic acid (hexanedioic acid), fumaric acid, and glutaric acid.

A particularly preferred embodiment according to the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier, wherein the acidifier is adipic acid.

A particularly preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is adipic acid.

A particularly preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and adipic acid.

The drug solution is transported to the duodenum after the stomach passage. The duodenum is the site of action. This passage is—at least in the fasted state—connected with an increase of the pH from about 2 to about 6. The drug dose has to remain in the solution, i.e. the drug should not precipitate. This effect can be achieved by the addition of a polymeric precipitation inhibitor. Thus, the polymeric precipitation inhibitor inhibits the crystallization of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and functions as a crystallization inhibitor.

Polymeric precipitation inhibitors are polymers capable to stabilize the supersaturation stage of the drug, i.e. they are able to prevent nucleation of the drug molecules or the growing of the initially formed drug particles, which is achieved by covering the surface of the drug particles, thereby preventing particle-particle interaction, or by enhancing the viscosity of the suspension medium. The ability of precipitation inhibitors to kinetically stabilize the supersaturated state of the drug is thought to result from intermolecular interactions between the drug and polymer in solution (e.g. via hydrogen bonding or hydrophobic interactions), the ability of the polymer to sterically hinder the crystallization process or from increasing the viscosity of the suspension medium.

The saturation solubility of said compound is low at a pH value in the duodenum (example 5 and FIG. 4). However, the compound is soluble in the acidic environment of the stomach supported by the addition of the acidifier leading to supersaturated solutions before entering the small intestine. This solution is stabilized by the addition of polymeric precipitation inhibitor which can also act as a binder. When reaching the duodenum the pH value of the solution raises thereby reducing the solubility of the compound. However, in this aqueous solution, the polymeric precipitation inhibitor and/or the binder exert their action by decelerating the precipitation or crystallization of the drug through complexation. Apart from that, the binder/polymeric precipitation inhibitor increases the viscosity in the medium which further intensifies the effect.

Thus, the systemic formulation according to the invention can further comprise a polymeric precipitation inhibitor. Thus, the excipient can be a polymeric precipitation inhibitor.

The term "polymeric precipitation inhibitor" refers to a material that decelerates the precipitation or crystallization of a drug.

"polymeric precipitation inhibitor" includes cellulose derivatives, starch derivatives, dextran/dextrin derivatives, polyether derivatives, polyvinyl derivatives, polyacrylic acid derivatives and poly amine derivatives, polysulfonic acid derivatives and a combination thereof.

In some embodiments "polymeric precipitation inhibitor" is selected from the group comprising or consisting of:

- cellulose derivatives including but not limited to microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phthalate), hydroxypropyl methylcellulose acetate succinate (HPMCAS, hypromellose acetate succinate);
- starch derivatives including but not limited to hydroxyethyl starch, hydroxypropyl starch (HPS) and pregelatinized starch;
- dextran/dextrin derivatives including but not limited to cyclodextran (i.e., cycloisomalto-heptaose (CI-7), cycloisomalto-octaose (CI-8), cycloisomalto-nonaose (CI-9)), hydroxypropyl dextran, maltodextrin, α-/β-/γ-cyclodextrin, 2-hydroxyethyl-β-cyclodextrin, 2-hydroxypropyl-β-cyclodextrin (HPβCD), sulfobuthylether-β-cyclodextrin sodium salt, methylated-β-cyclodextrin, 2-hydroxypropyl-γ-cyclodextrin;

polyether derivaitves including but not limited to polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl derivatives including but not limited to polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), polyacrylic acid derivatives including but not limited to poly(acrylic acid) (PAA), poly(acrylamide/acrylic acid) (PAC-AC), polymethylacrylate (PMA), polymethacrylic acid, poly(methacrylic acid/methyl methacrylate), poly(methacrylic acid/ethyl acrylate);

polyamine derivatives including but not limited to polyethylene imine (PEI), polyallylamine hydrogen chloride, polydiallydimethyl ammonium chloride, and poly (2-ethyl-2-oxazoline);

polysulfonic acid derivatives including but not limited to polystyrensulfonic acid (PSSA); and a combination of at least two of the above-mentioned polymeric precipitation inhibitors.

Preferably, the "polymeric precipitation inhibitor" is selected from the group comprising or consisting of: microcrystalline cellulose (MCC), cellulose acetate phthalate (CAP), cellulose aceate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), hydroxyethyl starch, hydroxypropyl starch (HPS) and pregelatinized starch, cyclodextran (i.e., cycloisomalto-heptaose (CI-7), cycloisomalto-octaose (CI-8), cycloisomalto-nonaose (CI-9)), hydroxypropyl dextran, maltodextrin, α-/β-/γ-cyclodextrin, 2-hydroxyethyl-β-cyclodextrin, 2-hydroxypropyl-β-cyclodextrin (HPβCD), sulfobuthylether-ρ-cyclodextrin sodium salt, methylated-β-cyclodextrin, 2-hydroxypropyl-γ-cyclodextrin, polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO—PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethylacrylate (PMA), polymethacrylic acid, poly(methacrylic acid/methyl methacrylate), poly(methacrylic acid/ethyl acrylate), polyethylene imine (PEI), polyallylamine hydrogen chloride, polydiallydimethyl ammonium chloride, poly(2-ethyl-2-oxazoline), polystyrensulfonic acid (PSSA); and a combination of at least two of the above-mentioned polymeric precipitation inhibitors.

More preferably, the"polymeric precipitation inhibitor" is selected from the group comprising or consisting of: microcrystalline cellulose (MCC), cellulose acetate phthalate (CAP), cellulose aceate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), polyethylene glycol (PEG), polyethylene oxide (PEO), polyether polyol, poly(propylene glycol) bis (2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethylacrylate (PMA), polymethacrylic acid, poly(methacrylic acid/methyl methacrylate), poly(methacrylic acid/ethyl acrylate), and a combination of at least two of the above-mentioned polymeric precipitation inhibitors.

More preferably, suitable polymeric precipitation inhibitors include L-hydroxypropyl cellulose, hydroxypropyl cellulose, a combination of L-hydroxypropyl cellulose and hydroxypropyl cellulose, polyethylene glycol (PEG), poly (ethylene oxide)-poly (propylene oxide)-poly (ethylene oxide) (=poloxamer), polyvinyl alcohol (PVA), polyvinylpyrrolidone (PVP), carboxymethyl cellulose (CMC), methylcellulose (MC), hydroxyethylcellulose (HEC), hydroxypropylmethylcellulose (HPMC), ethylcellulose (EC), polyvinyl caprolactam-polyvinyl acetate-polyethylene glycol graft copolymer (Soluplus®), and/or sodium carboxymethyl cellulose. Still more preferably, the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative. More preferably, the polymeric precipitation inhibitor is polyvinyl caprolactam-polyvinyl acetate-polyethylene glycol graft copolymer (Soluplus®), a cellulose, a cellulose derivative, or a combination of cellulose and a cellulose derivative.

Preferably, the cellulose is microcrystalline cellulose (MCC) and the cellulose derivative is selected from the group consisting of microcrystalline cellulose (MCC), cellulose acetate phthalate (CAP), cellulose aceate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate).

Even more preferably, the polymeric precipitation inhibitor is selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose. Most preferably, the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose. The combination of L-hydroxypropyl cellulose and hydroxypropyl cellulose acts as polymeric precipitation inhibitor and disintegrant so that the amount of the disintegrant can be reduced.

The systemic formulations as disclosed herein and especially the systemic formulations for oral administration contain as polymeric precipitation inhibitor most preferably polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose.

The systemic formulations as disclosed herein and especially the systemic formulations for oral administration comprise most preferably at least one acidifier and/or at least one polymeric precipitation inhibitor.

The systemic formulations as disclosed herein and especially the systemic formulations for oral administration contain most preferably adipic acid as acidifier and polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose as polymeric precipitation inhibitor.

An embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a polymeric precipitation inhibitor.

An embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder/polymeric precipitation inhibitor, and wherein the polymeric precipitation inhibitor is selected from the group comprising or consisting of cellulose and cellulose derivatives.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor selected from the group comprising or consisting of polyvinyl alcohol (PVA), polyvinyl caprolactam-polyvinyl acetate-polyethylene glycol graft copolymer (Soluplus®), cellulose and cellulose derivative.

An embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose and/or hydroxypropyl cellulose.

An embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and/or hydroxypropyl cellulose.

An embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and L-hydroxypropyl cellulose and/or hydroxypropyl cellulose.

The systemic formulation according to the invention can comprise a binder. Thus, the excipient can be a binder. Binders are characterized as substances binding or "gluing" powders to each other and they consequently serve as "glue" in the formulation. Suitable binders include sugar, such as sucrose; polysaccharides such as xanthan gum, guar gum, carrageenan, starches derived from wheat, corn, rice and potatoes, and preagglutinated (modified) starch derived from wheat, corn, rice and potatoes, sodium starch glycolate; natural gums such as acacia gum, gelatin and tragacanth; derivatives of sea weed such as alginic acid, sodium alginate and ammonium calcium alginate, cellulose or derivative thereof such as hydroxypropyl cellulose, L-hydroxypropyl cellulose (low-substituted hydroxypropyl cellulose), methyl cellulose and sodium carboxymethylcellulose and hydroxypropyl methylcellulose, or polyvinylpyrrolidone in particular povidone K25. Preferably the binder is a polymer, more preferably a gel-forming polymer, still more preferably the binder is a cellulose or a derivative thereof, still more preferably L-hydroxypropyl cellulose, and most preferably a combination of L-hydroxypropyl cellulose and hydroxypropyl cellulose. The combination of L-hydroxypropyl cellulose and hydroxypropyl cellulose also acts as polymeric precipitation inhibitor and disintegrant.

Hydroxypropyl cellulose is a partially substituted poly (hydroxypropyl) ether of cellulose. It may contain not more than 0.6% of silica or another suitable anticaking agent. Hydroxypropyl cellulose is commercially available in a number of different grades that have various solution viscosities. Molecular weight ranges from 50000-1250000. Hydroxypropylcellulose is partly O-(2-hydroxypropylated) cellulose. It contains 53.4% to 80.5% of hydroxypropoxy groups with reference to the dried substance. The average grade of polymerization ranges from 200 to 300. The molar grade of substitution is around 4. "Low-substituted hydroxypropyl cellulose" (L-HPC or LHPC) is a low-substituted poly(hydroxypropyl) ether of cellulose. It is commercially available in a number of different grades that have different particle sizes and substitution levels.

Low-substituted hydroxypropyl cellulose contains 5% to 16% hydroxypropoxy groups with reference to the dried substance. The molar grade of substitution is <1. In particular low-substituted hydroxypropyl cellulose is a low-substituted O-(2-hydroxypropylated) cellulose contains not less than 5.0% and not more than 16.0% of hydroxypropoxy groups ($—OCH_2CHOHCH_3$), calculated on the dried basis.

"Polyvinyl caprolactam-polyvinyl acetate-polyethylene glycol graft copolymer (PCL-PVAc-PEG) (Soluplus®)" has the following chemical structure:

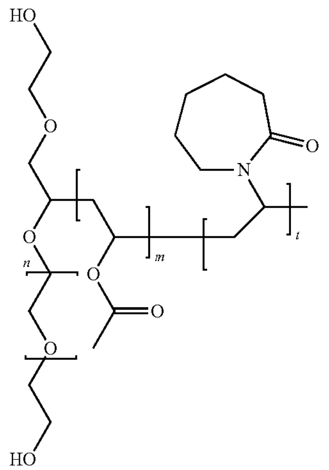

"Povidone" is synonymously used for polyvinylpyrrolidone (PVP).

Polyvinylpyrrolidone consists of linear polymers of 1-ethenylpyrollidin-2-one. The different types of polyvinylpyrrolidone are characterized by the viscosity of their solutions, expressed by the K value. Polyvinylpyrrolidone is present as a white to yellowish white powder or flake and is readily soluble in water. The K value is a common classification in the plastics industry and is directly related to the average molar mass of the polymer. This makes it possible to deduce indirectly from the K value the degree of polymerization and thus the chain length. Povidone K25, povidone K30 or povidone K90 is commercially available. Preferably, povidone K25 is used as a binder. The approximate average molecular weight of povidone K25 is 30,000 in the range of 28,000 g/mol (KDa) to 34,000 g/mol (KDa).

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder, and wherein the binder is polyvinylpyrrolidone.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polyvinylpyrrolidone.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder, wherein the binder is polyvinylpyrrolidone, and wherein the polyvinylpyrrolidone is povidone K25.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and povidone K25.

Moreover, the systemic formulation according to the invention can comprise a binder and/or a polymeric precipitation inhibitor.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and polymeric precipitation inhibitor. Preferably, at least one excipient functions as a binder and a polymeric precipitation inhibitor at the same time. Thus, at least one excipient is a binder and polymeric precipitation inhibitor.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one compound being a binder and polymeric precipitation inhibitor.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one binder and at least one polymeric precipitation inhibitor.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a derivative or combination of cellulose derivatives.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a derivative or combination of cellulose derivatives.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropylcellulose.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose.

An embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of a binder and polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose or hydroxypropyl cellulose or a combination of L-hydroxypropyl cellulose and hydroxypropyl cellulose, and wherein the binder is polyvinylpyrrolidone.

An embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose and at least one binder selected from the group L-hydroxypropyl cellulose, hydroxypropyl cellulose and hydroxypropyl cellulose, and/or polyvinylpyrrolidone.

A particularly preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and/or at least one excipient is a polymeric precipitation inhibitor, and wherein the binder/polymeric precipitation inhibitor is a cellulose, a cellulose derivative, a combination of cellulose and a cellulose derivative or combination of cellulose derivatives, And the binder is cellulose, a cellulose derivative, a combination of cellulose and a derivative or combination of cellulose derivatives, and/or povidone K25.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a derivative or combination of cellulose derivatives, and the binder is cellulose, a cellulose derivative, a combination of cellulose and a derivative or combination of cellulose derivatives, and/or povidone K25.

Another preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and/or at least one excipient is a polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose, and wherein the binder is L-hydroxypropyl cellulose, hydroxypropyl cellulose, a combination of L-hydroxypropyl cellulose and hydroxypropyl cellulose, and/or povidone K25.

Another preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose, and wherein the binder is L-hydroxypropyl cellulose, hydroxypropyl cellulose, a combination of L-hydroxypropyl cellulose and hydroxypropyl cellulose, and/or povidone K25.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and/or at least one excipient is a polymeric precipitation inhibitor, and wherein thpolymeric precipitation inhibitor is polyvinyl alcohol (PVA), polyvinyl caprolactam-polyvinyl acetate-polyethylene glycol graft copolymer (Soluplus®), L-hydroxypropyl cellulose hydroxypropyl cellulose, or a combination of L-hydroxypropyl cellulose and hydroxypropyl cellulose, wherein the binder is povidone K25.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose, wherein the binder is povidone K25.

The data of the pharmacokinetic study in human confirm the high relative bioavailability of compound (I). A high relative bioavailability in this context has to be understood in comparison to the animal studies which have been performed previously.

The in vivo inhibition of small intestinal tissue transglutaminase (TG2) by the compound according to formula (I) was demonstrated in the polyinosinic:polycytidylic acid (poly(I:C)) model of small intestinal inflammation. Activation of intestinal TG2 was induced within 2-4 hours after administration of poly(I:C). Inflammation was most pronounced in the jejunum and colon. TG2 activity was upregulated in the small intestine up to 2-fold and 4-fold, respectively, as occurs in active celiac disease. Administration of the TG2 inhibitor as plain, unformulated compound was safe and reduced the activity of intestinal TG2 to normal levels. This was paralleled by subdued intestinal inflammation (Encalada Ventura et al. 2018).

The addition of an acidifier ensures the complete dissolution of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof in the stomach but the pH in the duodenum increases from 2 to 6, and thus the drug can precipitate before it reaches the duodenum or in the duodenum. In order to ensure a complete dissolution of said compound, a transport into the duodenum, and a drug in a dissolved form in the duodenum the formulation according to the invention contains preferably an acidifier, and/or a polymeric precipitation inhibitor.

The pharmacokinetic studies show that (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate is absorbed in the duodenum and a low dose of 20-50 mg is sufficient to achieve a therapeutic effective drug concentration in human (example 3, FIG. 1).

Moreover, side effects related to potential off-target actions were not observed in humans even at doses of up to 500 mg. As aforementioned, this is particularly surprising due to the fact that TG2 is ubiquitously expressed in almost all cell types and cell compartments, it is present on the cell surface and gets secreted to the extracellular matrix, and is present in various organs, and thus it could be envisioned that off-target effects would be most likely.

Thus, the systemic formulation according to the invention can comprise an acidifier and/or a polymeric precipitation inhibitor. Preferably, the systemic formulation comprises an acidifier and a polymeric precipitation inhibitor.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and polymeric precipitation inhibitor.

A preferred embodiment of the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier and at least one polymeric precipitation inhibitor.

A preferred embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid and at least one polymeric precipitation inhibitor.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and polymeric precipitation inhibitor, and wherein the acidifier is selected from the group comprising or consisting of adipic acid, fumaric acid, and glutaric acid; and the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and polymeric precipitation inhibitor, and wherein the acidifier is adipic acid, and the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier and at least one polymeric precipitation inhibitor, wherein the acidifier is adipic acid, and the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose.

A preferred embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier the acidifier is selected from the group comprising or consisting of adipic acid, fumaric acid, and glutaric acid; and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose.

A preferred embodiment of the invention is thus related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2- oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and polymeric precipitation inhibitor, and wherein the acidifier is adipic acid, and the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, and/or at least one polymeric precipitation inhibitor, and wherein the acidifier is adipic acid, and the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose.

A systemic formulation for use in the prophylaxis and/or treatment of coeliac disease containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation further comprises at least one excipient, wherein at least one excipient is selected from the group comprising or consisting of acidifier and polymeric precipitation inhibitor, wherein the acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

A systemic formulation for use in the prophylaxis and/or treatment of coeliac disease containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation further comprises at least one excipient, wherein at least one excipient is selected from the group comprising or consisting of acidifier and binder, wherein the acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate, and wherein the binder is selected from the group consisting of sugar, such as sucrose; polysaccharides such as xanthan gum, guar gum, carrageenan, starches derived from wheat, corn, rice and potatoes, and preagglutinated starch derived from wheat, corn, rice and potatoes, sodium starch glycolate; polyacrylic acids; natural gums such as acacia gum, gelatin and tragacanth; derivatives of sea weed such as alginic acid, sodium alginate and ammonium calcium alginate, cellulose or derivative thereof such as hydroxypropyl cellulose, L-hydroxypropyl cellulose, methyl cellulose and sodium carboxymethylcellulose and hydroxypropyl methylcellulose, or polyvinylpyrrolidone.

The systemic formulation for use in the prophylaxis and/or treatment of coeliac disease according to the invention can comprise an acidifier, a polymeric precipitation inhibitor, and/or a binder.

An embodiment for use in the prophylaxis and/or treatment of coeliac disease according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor and binder.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one acidifier, at least one polymeric precipitation inhibitor and at least one binder.

A more preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one acidifier, at least one polymeric precipitation inhibitor and at least one binder, wherein the acidifier is adipic acid, the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose, and wherein the binder is polyvinylpyrrolidone.

The systemic formulation according to the invention can comprise a disintegrant. Thus, the excipient can be a disintegrant. The term "disintegrant" refers to materials added to the composition in order to support disintegration of the formulation and release of the active pharmaceutical ingredient. Suitable disintegrants include starches, modified starches which are soluble in cold water, such as sodium carboxymethyl starch; cellulose derivatives such as methylcellulose and sodium carboxymethylcellulose, microcrystalline cellulose and crosslinked microcrystalline cellulose such as sodium croscarmellose; alginates such as alginic acid and sodium alginate; clays such as bentonites and foaming mixtures; effervescent compounds such as combinations of citric acid, tartaric acid, sodium citrate, disodium hydrogen citrate, monosodium citrate, sodium and/or potassium hydrogen carbonate that react in the presence of water to give carbon dioxide. Preferably, the disintegrant is sodium croscarmellose.

An embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a disintegrant.

An embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one disintegrant.

The systemic formulation according to the invention can comprise an acidifier, a binder/polymeric precipitation inhibitor, and/or a disintegrant.

An embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, a polymeric precipitation inhibitor, binder and disintegrant.

The systemic formulation according to the invention can comprise a lubricant/glidant. The excipient can thus be a lubricant/glidant. Lubricants/glidants are materials preventing caking and improving the flow characteristics of granulates so that the flow is smooth and uniform, and reducing the friction between the surfaces in direct contact in order to allow for the tablet, granulate, etc. to be released from the casting mold or pressing mold, after compression, by reducing the friction.

Suitable lubricants/glidants include sodium benzoate, metallic stearate such as magnesium stearate, calcium stearate, or potassium stearate, stearic acid, high melting point waxes, inorganic lubricants/glidants such as silicon dioxide and talc and other such as sodium oleate, and polyethylene glycols. Preferably, the lubricant/glidant is talc or silicon dioxide. Due to the fact that lubricants/glidants have to be present on the surface of the granules as well as between the granules and parts of the equipment they are typically added during the last step prior to encapsulation or compression.

A preferred embodiment of the invention is therefore directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a lubricant/glidant.

The systemic formulation according to the invention can comprise or consist of an acidifier, a polymeric precipitation inhibitor, a binder and/or a lubricant/glidant.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder and lubricant/glidant.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, and lubricant/glidant.

The systemic formulation according to the invention can comprise or consist of an acidifier, a polymeric precipitation inhibitor, a binder, a disintegrant, and/or a lubricant/glidant.

A preferred embodiment according to the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, disintegrant, and lubricant/glidant.

Furthermore, the systemic formulation according to the invention can also comprise as an excipient diluents/fillers/binders, sweetening agents, flavoring agents, buffering agents, antioxidants, emulsifiers, solubilizer/wetting agent and/or preservatives.

A suitable diluent/filler/binder is a substance which usually forms the largest part of the composition or dosage form. A suitable diluent/filler/binder includes sugars such as lactose, sucrose, mannitol and sorbitol; starches derived from wheat, corn, rice and potatoes; and cellulose such as microcrystalline cellulose, calcium hydrogen phosphate dihydrate, and calcium sulfate. Preferably, the diluent/filler/binder is cellulose and/or mannitol. Most preferably, the diluent/filler/binder is microcrystalline cellulose and/or mannitol.

Preferably, the diluent/filler/binder is microcrystalline cellulose when the formulation is a tablet, and the diluent/filler/binder is mannitol when the formulation is capsule.

The addition of mannitol further increases the porosity and therefore wettability of the granules. The systemic formulation for use in the prophylaxis and/or treatment of coeliac disease according to the invention can comprise a diluent/filler/binder. A preferred embodiment according to the invention is directed to systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and least one excipient, wherein at least one excipient is a diluent/filler/binder.

The systemic formulation for use in the prophylaxis and/or treatment of coeliac disease according to the invention can comprise or consists of an acidifier, a polymeric precipitation inhibitor, a binder, a disintegrant, a lubricant/glidant and/or a diluent/filler/binder. An embodiment of the invention is directed to a formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, disintegrant, lubricant/glidant and/or diluent/filler/binder.

An embodiment of the invention is directed to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one a binder, at least one disintegrant, at least one lubricant/glidant and at least one diluent/filler/binder.

The preferred preparations are provided in an administrable form suitable for oral application, such as tablets such as uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules. More preferably, the oral formulation is a tablet or capsule. Uncoated and coated tablets, and capsules, either hard or soft are the most preferred pharmaceutical formulations.

An embodiment of the present invention is directed to a systemic formulation for use in the prophylaxis and/or treatment of coeliac disease containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is a tablet, coated tablet, capsule, powder, or granule.

The systemic formulation according to the invention can comprise other ingredients such as unavoidable impurities, ingredients for the capsule including colorants of the capsule. Also in a tablet, a colorant as other ingredient can be present.

Furthermore, components used for coating a tablet are also encompassed by the term "other ingredients".

The shell of the capsule can comprise a colorant. As used herein, the term "colorant" includes pigments such as white pigments. The colorant can be among others iron oxide in particular iron(III)oxide, iron(II,III) oxide or hydrated ferric oxide or titanium dioxide.

"Tablet" means a compressed solid dosage form containing at least active pharmaceutical ingredient with suitable excipients. The tablet can be produced by compressing mixtures or granulates obtained by wet granulation, dry granulation or compaction, which are known to the one skilled in the art.

The term "capsule" refers to a special container or shell composed of methylcellulose, polyvinyl alcohols or gelatins or denatured gelatins or starches, in which the active agents can be enclosed. Typically, hard shell capsules are prepared from hydroxypropyl methylcellulose or from mixtures of porcine bone and skin gelatins having comparatively high gel strength. The shell of the capsule can contain small amounts of colorants, opacifiers, softening agents and preservatives. "Soft shell capsules" contains gelatin as a basic polymer, one or more softening agents such as glycerol or sorbitol in a higher amount as well as water. In general, the amount of the softening agent is 20-30% by weight of the capsule shell, the amount of the gelatin is 40-45% by weight of the capsule shell, and amount of water is 30-35% by weight of the capsule shell. After the drying of the capsule, the amount of water is 7-8% by weight of the capsule shell.

The capsule shell can comprise gelatine, hydroxypropyl methylcellulose (HMPC), polysaccharides such as starch, and carrageenan; and/or synthetic polymers such as copolymers of polyvinylalcohol. Furthermore, the shell of the capsule can comprise a colorant. As used herein, the term "colorant" includes pigments such as white pigments. The colorant can be among others iron oxide in particular iron(III)oxide, iron(II,III) oxide or hydrated ferric oxide, titanium dioxide, natural dyes, azo and xanthane compounds. Moreover, the capsule shell may comprise a preservative such as p-hydroxybenzoic acid esters or means to improve the flavour such as ethylvanillin. In addition, the capsule shell can comprise a surfactant such a sodium lauryl sulfate.

"Powders" for compositions refer to powder mixtures/blends containing the active components and suitable excipients which can be suspended in water or juices prior to use. Spherical-shaped granules are also referred to pellets or beads.

"Granules" refer to dry and solid grains. Each grain represents an agglomerate of powder particles.

Coated Drug

While the wrapping or embedding method drug particles are treated, the coating method is related to the dosage form itself. Tablets, the center of dragees or capsules are coated with coating layer, wherein excipients such as derivative of cellulose, cellulose ether such as hydroxypropyl methylcellulose (HMPC), synthetic polymers, corn protein zein or other polysaccharides. The coating can further comprise colorants such as titanium dioxide, iron(III)oxide, iron(II,III) oxide or hydrated ferric oxide, lactose monohydrate, and or carnauba wax. Also capsule can be coated.

Sustained-release-type formulations are known in the state of the art for the provision of a controlled release rate of any one or more components or active components, in order to optimize the therapeutic effect, i.e. the inhibitory activity and the like. The pharmacological optimal concentration is guaranteed for a certain time above the period of effect of a single dosage. Suitable dosage forms for sustained release include layered tablets containing layers with varying degradation rates or controlled release polymeric matrices impregnated with the active components and in the form of a tablet or capsule containing such impregnated or encapsulated porous polymeric matrices. A sustained-release type formulation would impede a fast release of the compound. Herein, it is desired that a high concentration of the drug is quickly released to the target site after the administration. Consequently, sustained-release type formulations are not preferred and should actually be avoided for the purposes of the present invention, because preliminary results indicate that such formulations cannot provide the required high drug concentration according to the present invention.

The term "fast release" as used herein refers to a systemic formulation for targeting the duodenal tract containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate as pharmaceutically active ingredient. Therefore, the term "systemic formulation for fast release" refers to a systemic formulation for release and preferably for complete release of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in the duodenal tract preferably within 30 minutes, more preferably within 25 minutes, still more preferably within 20 minutes, and still more preferably within 15 minutes.

The systemic formulation according to the invention can be in form of a capsule or tablet, i.e. active agent and the excipient can be filled in the capsule. An embodiment according to the invention is a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is in form of a capsule or tablet.

A preferred embodiment according to the invention is a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier and polymeric precipitation inhibitor, wherein the systemic formulation is in form of a capsule or tablet.

Another preferred embodiment according to the invention is a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, and binder, wherein the systemic formulation is in form of a capsule or tablet.

Another preferred embodiment according to the invention is a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, and at least one binder, wherein the systemic formulation is in form of a capsule or tablet.

Another preferred embodiment according to the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least at excipient, wherein at least one excipient is selected from the group comprising or consisting of acidifier, polymeric precipitation inhibitor, binder, disintegrant, and lubricant/glidant, wherein the systemic formulation is in form of a capsule or tablet.

Another preferred embodiment according to the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one binder, at least one disintegrant, and at least one lubricant/glidant, wherein the systemic formulation is in form of a capsule or tablet.

Another preferred embodiment according to the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, disintegrant, lubricant/glidant, and diluent/filler/binder, wherein the systemic formulation is in form of a capsule or tablet.

Another preferred embodiment according to the invention is related to a systemic formulation for use in the prophylaxis and/or treatment of coeliac disease containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one binder, at least one disintegrant, at least one lubricant/glidant, and at least one diluent/filler/binder, wherein the systemic formulation is in form of a capsule or tablet.

The preferred pharmaceutical formulation is for oral administration. Therefore, preferred pharmaceutical formulations are systemic formulation in form of an enteral formulation for oral administration. Consequently, especially capsules and tablets are the most preferred enteral or parenteral formulation for oral administration and especially these capsules and tablets which ensure fast release of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, and thereby ensuring high drug concentrations.

Moreover, pharmaceutical formulations for oral administration containing adipic acid are preferred. More preferred are systemic formulations in form of an enteral or parenteral formulation for oral administration containing adipic acid. Most preferred are capsules and tablets for oral administration containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and adipic acid.

Furthermore, in order to further improve the performance of the formulation the specific PSD (particle size distribution), and/or PSR (particle size range) can be adapted.

Therefore, an embodiment according to the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

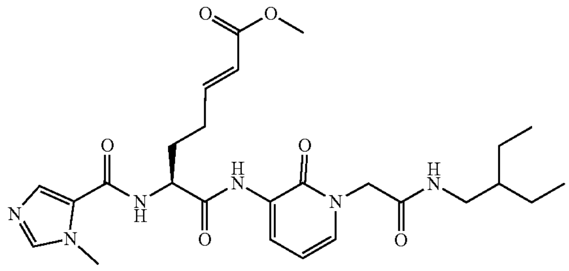
, or a solvate, a hydrate or a pharmaceutically acceptable salt of formula (I) for use in the prophylaxis and/or treatment of coeliac disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm It is furthermore preferred that the particle size of the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is within the range of 0.1 μm to 100 μm, preferably in the range of 0.5 μm to 50 μm and more preferably in the range of 1.0 μm to 20 μm. Thus, the particle size range (PSR) of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is from 0.1 μm to 100 μm, from 0.5 μm to 50 μm, or from 1.0 μm to 20 μm. Preferably, the particle size of the drug according to formula (I) is ≤10 μm.

Another preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm.

Therefore, an embodiment according to the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

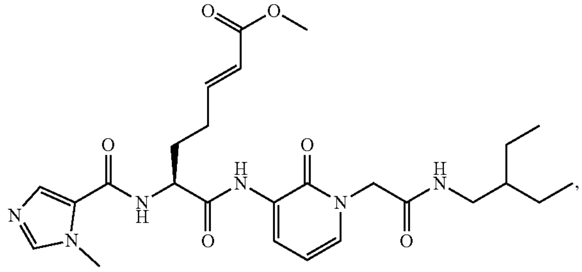
, or an enantiomer, a solvate, a hydrate or a pharmaceutically acceptable salt of formula (I) for use in the prophylaxis and/or treatment of coeliac disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95)≤25 μm, wherein (S,E)-methyl-7-(1-(2-(2-ethylbutylamino)-2-oxoethyl)-2-oxo-1,2-dihydro-1-pyridin-3-ylamino)-6-(1-methyl-1H-imidazole-5-carboxamido)-7-oxohept-2-enoate is preferably micronized.

Moreover it is preferred that the particle size distribution of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is characterized by d(0.1) from 0.1 to 5 μm, d(0.5) from 0.3 to 10 μm, d(0.95) from 3 to 25 μm, more preferably d(0.1) from 0.2 to 3 μm, d(0.5) from 0.4 to 7.5 μm and d(0.95) from 2 to 15 μm, and most preferably d(0.1) from 0.3 to 3 μm, d(0.5) from 0.5 to 5 μm and d(0.95) from 1 to 10 μm.

The particle size distribution is measured by laser light diffraction (Malvern analysis, sample dispersed in n-hexane and sorbitane monooleate). Thereby, the laser light is scattered in dependence of the particle size. A diffraction pattern results. From the angle dependent scattered light intensity, the particle size can be calculated.

The parameter d(0.1) refers to the diameter at which 10% of the total volume of particles in the sample is comprised of particles with a diameter less than the indicated value or range of values when analysed by laser diffraction (Malvern analysis, sample dispersed in n-hexane and sorbitane monooleate). Thus d(0.1)=0.1 to 5 μm means that the upper limit of the particle size range defining the 10% of smallest particles in the sample is between 0.1 μm to 5 μm. Thus 10% of the total particles have a particle size of not more than d(0.1) meaning in this case that they have a maximum size of 0.1 μm to 5 μm.

Accordingly the parameter d(0.5) refers to the diameter at which 50% of the total volume of particles in the sample is comprised of particles with a diameter less than the indicated value or range of values when analysed by laser diffraction (Malvern analysis, sample dispersed in n-hexane and sorbitane monooleate). Thus d(0.5)=0.3 to 10 μm means that the upper limit of the particle size range defining the 50% of smallest particles in the sample is between 0.3 μm to 10 μm. Thus 50% of the total particles have a particle size of not more than d(0.5) meaning in this case that they have a maximum size of 0.3 μm to 10 μm.

Accordingly the parameter d(0.95) refers to the diameter at which 95% of the total volume of particles in the sample is comprised of particles with a diameter less than the indicated value or range of values when analysed by laser diffraction (Malvern analysis, sample dispersed in n-hexane and sorbitane monooleate). Thus d(0.95)=3 to 25 μm means that the upper limit of the particle size range defining the 95% of smallest particles in the sample is between 3 μm to 25 μm. Thus 95% of the total particles have a particle size of not more than d(0.95) meaning in this case that they have a maximum size of 3 μm to 25 μm.

Another embodiment of the present invention is directed to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-1-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) ≤25 μm.

A preferred embodiment of the present invention is directed to a systemic formulation for use in the prophylaxis and/or treatment of coeliac disease comprising or consisting (S,E)-methyl-7-(1-(2-(2-ethylbutylamino)-2-oxoethyl)-2-oxo-1,2-dihydro-1-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein (S,E)-methyl-7-(1-(2-(2-ethylbutylamino)-2-oxoethyl)-2-oxo-1,2-dihydro-1-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A more preferred embodiment according to the invention is a systemic formulation for use in the prophylaxis and/or treatment of coeliac disease comprising or consisting (S,E)-methyl-7-(1-(2-(2-ethylbutylamino)-2-oxoethyl)-2-oxo-1,2-dihydro-1-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-1-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A still more preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.2 to 3 μm, d(0.5) from 0.4 to 7.5 μm and d(0.95) from 2 to 15 μm.

A even more preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, sodium croscarmellose, and talc, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.2 to 3 μm, d(0.5) from 0.4 to 7.5 μm and d(0.95) from 2 to 15 μm.

A particularly preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, sodium croscarmellose, talc, gelatine and titanium dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate have a particle size distribution which is defined by d(0.1) from 0.1 to 5 μm, d(0.5) from 0.3 to 10 μm, and d(0.95) from 3 to 25 μm.

Another particularly preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, povidone K25, sodium croscarmellose, microcrystalline cellulose and silicon dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof have a particle size distribution which is defined by d(0.1) from 0.1 to 5 μm, d(0.5) from 0.3 to 10 μm, and d(0.95) from 3 to 25 μm.

Therefore, an embodiment according to the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

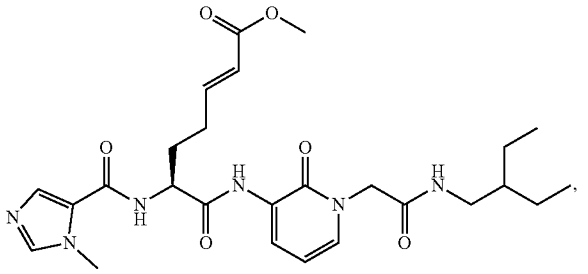

or an enantiomer, a solvate, a hydrate or a pharmaceutically acceptable salt of formula (I) for use in the prophylaxis and/or treatment of coeliac disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles, have a particle size range from 0.1 to 100 μm, and a particle size distribution which is defined by d(0.95)≤25 μm.

Thus, preferred are systemic formulations containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxo-hept-2-enoate or an enantiomer, a solvate, a hydrate or a pharmaceutically acceptable salt thereof for use in the prophylaxis and/or treatment of coeliac disease, wherein the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxo-hept-2-enoate or enantiomer, solvate, hydrate or pharmaceutically acceptable salt thereof is in form of particles having a particle size distribution which is defined by d(0.95)≤25 μm.

A preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

A more preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, hydroxypropyl cellulose, mannitol, sodium croscarmellose, and talc, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

A particularly preferred embodiment according to the invention is a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, hydroxypropyl cellulose, mannitol, sodium croscarmellose, talc, gelatine and titanium dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

Another particularly preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, povidone K25, sodium croscarmellose, microcrystalline cellulose and silicon dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

The systemic formulation can contain (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or enantiomer, solvate, hydrate, or a pharmaceutically acceptable salt in an amount of at least 0.01 mg, preferably at least 0.1 mg, more preferably at least 0.5 mg, even more preferably at least 1 mg, even more preferably at least 2 mg, even more preferably at least 3 mg, even more preferably at least 4 mg, even more preferably at least 5 mg, even more preferably 0.01 mg to 1000 mg, even more preferably 0.05 mg to 900 mg, even more preferably 0.10 mg to 800 mg, still more preferably 0.2 mg to 700 mg, still more preferably 0.3 mg to 600 mg, still more preferably 0.4 mg to 500 mg, still more preferably 0.5 mg to 500 mg, still more preferably 0.6 mg to 450 mg, still more preferably 0.7 mg to 400 mg, still more preferably 0.8 mg to 375 mg, still more preferably 0.9 mg to 350 mg, still more preferably 1.0 mg to 300 mg, still more preferably 1.25 mg to 300 mg, still more preferably 1.5 mg to 275 mg, still more preferably 1.75 mg to 250 mg, still more preferably 2.0 mg to 225 mg, still more preferably 2.25 mg to 220 mg, still more preferably 2.5 mg to 220 mg, still more preferably 2.75 mg to 215 mg, still more preferably 3.0 mg to 210 mg, still more preferably 3.75 mg to 205 mg, still more preferably 4.0 mg to 205 mg, 4.5 mg to 200 mg, most preferably 5 mg to 200 mg per formulation.

The systemic formulation can contain (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or enantiomer, solvate, hydrate or a pharmaceutically acceptable salt, solvate or hydrate in an amount of 0.1 wt % to 99 wt %, preferably 0.2 wt % to 90 wt %, more preferably 0.3 wt % to 85 wt %, even more preferably 0.4 wt % to 80 wt %, even more preferably 0.5 wt % to 75 wt %, even more preferably 0.6 wt % to 70 wt %, even more preferably 0.7 wt % to 65 wt %, even more preferably 0.8 wt % to 60 wt %, even more preferably 0.9 wt % to 55 wt %, even more preferably 1 wt % to 50 wt %, even more preferably 1 wt % to 45 wt %, even more preferably 1.25 wt % to 45 wt %, even more preferably 1.5 wt % to 40 wt %, even more preferably 1.75 wt % to 35 wt %, even more preferably 2 wt % to 34 wt %, even more preferably 2.25 wt % to 33 wt %, even more preferably 2.5 wt % to 32 wt %, and most preferably 2.5 wt % to 31 wt %, even more preferably 2.5 wt % to 30.5 wt %, and even more preferably 2.6 wt % to 30.3 wt %, even more preferably 3 wt % to 30 wt %, even more preferably 3.5 wt % to 29 wt %, even more preferably 4 wt % to 28 wt %, even more preferably 4 wt % to 27 wt %, even more preferably 4.5 wt % to 27 wt %, and most preferably 5 wt % to 27 wt %. "Wt %" (weight percent") refers to the weight percent in the composition.

The amount of the acidifier can range from 0.1 wt % to 80 wt %, preferably from 0.5 wt % to 77.5 wt %, more preferably from 1 wt % to 75 wt %, more preferably from 1.5 wt % to 72.5 wt %, more preferably from 2 wt % to 70 wt %, more preferably from 2.5 wt % to 62.5 wt %, more preferably from 3 wt % to 57.5 wt %, more preferably from 3.5 wt % to 55 wt %, even more preferably from 4 wt % to 55 wt %, even more preferably from 4.5 wt % to 55 wt %, even more preferably from 5 wt % to 54 wt %, even more preferably from 5.5 wt % to 53 wt %, even more preferably from 6 wt % to 52 wt %, even more preferably from 6.5 wt % to 51 wt %, even more preferably from 7 wt % to 50 wt %, even more preferably from 8 wt % to 49 wt %, even more preferably from 8.5 wt % to 49 wt %, and most preferably from 9 wt % to 49 wt %. Moreover, the amount of the acidifier can range from 1.00 mg to 500 mg, more preferably from 1.25 mg 495 mg, still more preferably from 1.50 mg to 490 mg, still more preferably from 1.75 mg to 485 mg, still more preferably from 2.00 mg to 480 mg, still more preferably from 2.25 mg to 475 mg, still more preferably from 2.50 mg to 470 mg, still more preferably from 3.0 mg to 465 mg, still more preferably from 3.25 mg to 460 mg, still more preferably from 3.5 mg to 455 mg, even more preferably from 3.75 mg to 450 mg, even more preferably from 4.00 mg to 445 mg, even more preferably from 4.25 mg to 440 mg, still more preferably from 4.5 mg to 435 mg, still more preferably from 4.75 mg to 430 mg, still more preferably from 5.0 mg to 425 mg, still more preferably from 5.25 mg to 420 mg, still more preferably from 5.5 mg to 415 mg, still more preferably from 5.75 mg to 410 mg, still more preferably from 6.0 mg to 410 mg, still more preferably from 6.25 mg to 405 mg, still more preferably from 6.5 mg to 400 mg, still more preferably from 6.75 mg to 395 mg, still more preferably from 7.0 mg to 390 mg, still more preferably from 7.5 mg to 390 mg, still more preferably from 7.75 mg to 385 mg, still more preferably from 8.0 mg to 380 mg, still more preferably from 8.5 mg to 375 mg, still more preferably from 9 mg to 370 mg, still more preferably from 9 mg to 365 mg, still more preferably from 9 mg to 360 mg, still more preferably from 9 mg to 350 mg, still more preferably from 9 mg to 325 mg, still more preferably from 9 mg to 300 mg, still more preferably from 9 mg to 250 mg, still more preferably from 9 mg to 200 mg, and most preferably from 9 mg to 180 mg. Furthermore, a mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 15 to 0.1 m/m, preferably from 14.5 to 0.2 m/m, more preferably from 14.0 to 0.3 m/m, still more preferably from 13.5 to 0.4 m/m, still more preferably from 13.0 to 0.5 m/m, still more preferably from 12.5 to 0.6 m/m, still more preferably from 12.0 to 0.7 m/m, still more preferably from 11.75 to 0.8 m/m, still more preferably from 11.5 to 0.9 m/m, still more preferably from 11.5 to 1.0 m/m, still more preferably from 11.5 to 1.1 m/m, still more preferably from 11.5 to 1.2 m/m, still more preferably from 11.5 to 1.3 m/m, still more preferably from 11.5 to 1.4 m/m, still more preferably from 11.5 to 1.5 m/m, still more preferably from 11.5 to 1.6 m/m, still more preferably from 11.5 to 1.7 m/m, more preferably from 11.5 to 1.8 m/m, and most preferably from 2 to 1 m/m.

The amount of the binder/polymeric precipitation inhibitor can vary from 0.1 wt % to 40 wt %, preferably 0.5 wt % to 39 wt %, more preferably 1 wt % to 38 wt %, still more preferably 1.25 wt % to 38 wt %, still more preferably 1.5 wt % to 37 wt %, still more preferably 1.75 wt % to 36 wt %, still more preferably 2 wt % to 35 wt %, still more preferably 1.5 wt % to 34 wt %, still more preferably 1.6 wt % to 33 wt %, still more preferably 1.7 wt % to 32 wt %, still more preferably 1.8 wt % to 31 wt %, still more preferably 3.5 wt % to 30 wt %, still more preferably 4 wt % to 29 wt %, still more preferably 4.5 wt % to 28.5 wt %, most preferably 5 wt % to 28.5 wt %.

Furthermore, the amount of the polymeric precipitation inhibitor can range from 1 mg to 100 mg, preferably from 1.5 mg to 95 mg, more preferably from 2 mg to 92.5 mg, still more preferably 2.5 mg to 90 mg, still more preferably 3 mg to 87.5 mg, still more preferably 3.5 mg to 85 mg, still more preferably 4 mg to 82.5 mg, still more preferably 4.5 mg to 80 mg, still more preferably 5 mg to 77.5 mg, still more preferably 5.5 mg to 75 mg, 6 mg to 72.5 mg, still more preferably 6.5 mg to 70 mg, still more preferably 7 mg to 65 mg, still more preferably 7.5 mg to 62.5 mg, still more preferably 8 mg to 60 mg, even more preferably from 8.5 mg to 57.5 mg, even more preferably from 9 mg to 55 mg, even more preferably from 9.5 mg to 52.5 mg, even more preferably from 9.75 mg to 52.5 mg, and most preferably from 10 mg to 50 mg.

Furthermore, a mass ratio of the polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 10 m/m, preferably from 0.06 to 9.5 m/m, more preferably from 0.07 to 9.00 m/m, still more preferably from 0.08 to 8.5 m/m, still more preferably from 0.09 to 8.00 m/m, still more preferably from 0.1 to 7.5 m/m, still more preferably from 0.11 to 7.25 m/m, still more preferably from 0.12 to 7.00 m/m, still more preferably from 0.13 to 6.75 m/m, still more preferably from 0.14 to 6.5 m/m, still more preferably from 0.15 to 6.25 m/m, even more preferably from 0.16 to 6.00 m/m, even more preferably from 0.17 to 5.75 m/m, even more preferably from 0.18 to 5.5 m/m, even more preferably from 0.19 to 5.25 m/m, and most preferably from 0.2 to 5 m/m.

The amount of the binder can vary from 0 wt % to 40 wt %, preferably from 0 wt % to 35 wt %, more preferably from 0 wt % to 30 wt %, still more preferably from 0 wt % to 25 wt %, still more preferably from 0 wt % to 20 wt %, still more preferably from 0 wt % to 15 wt %, still more preferably from 0 wt % to 12 wt %, and most preferably from 0 wt % to 8.5 wt %.

Furthermore, the amount of the binder can range from 1.00 mg to 100 mg, preferably from 1.50 mg to 95 mg, more preferably from 2.00 mg to 92.5 mg, still more preferably 2.50 mg to 90 mg, still more preferably 3.00 mg to 87.5 mg, still more preferably 3.50 mg to 85 mg, still more preferably 4.00 mg to 82.5 mg, still more preferably 4.50 mg to 80 mg, still more preferably 5.00 mg to 77.5 mg, still more preferably 5.50 mg to 75 mg, 6.00 mg to 72.5 mg, still more preferably 6.50 mg to 70 mg, still more preferably 7.00 mg to 65 mg, still more preferably 7.50 mg to 62.5 mg, still more preferably 8.00 mg to 60 mg, even more preferably from 8.50 mg to 57.5 mg, even more preferably from 9.00 mg to 55.0 mg, even more preferably from 9.50 mg to 52.5 mg, even more preferably from 9.75 mg to 52.5 mg, and most preferably from 10 mg to 50 mg.

Furthermore, a mass ratio of the binder relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 to 10 m/m, preferably from 0.05 to 9.5 m/m, more preferably from 0.06 to 9.00 m/m, still more preferably from 0.07 to 8.50 m/m, still more preferably from 0.08 to 8.00 m/m, still more preferably from 0.09 to 7.5 m/m, still more preferably from 0.1 to 7.25 m/m, still more preferably from 0.11 to 7.00 m/m, still more preferably from 0.12 to 6.75 m/m, still more preferably from 0.13 to 6.50 m/m, still more preferably from 0.14 to 6.25 m/m, even more preferably from 0.15 to 6.00 m/m, even more preferably from 0.16 to 5.75 m/m, even more preferably from 0.17 to 5.50 m/m, even more preferably from 0.18 to 5.25 m/m, even more preferably from 0.19 to 5.5 m/m, even more preferably from 0.20 to 5 m/m, even more preferably from 0.20 to 4.5 m/m, even more preferably from 0.20 to 4 m/m, even more preferably from 0.20 to 3.5 m/m, even more preferably from 0.20 to 3 m/m, even more preferably from 0.20 to 2.5 m/m, and even more preferably from 0.20 to 2 m/m.

The amount of the disintegrant can vary from 0.1 wt % to 40 wt %, preferably from 1 wt % to 35 wt %, even more preferably from 2 wt % to 30 wt %, even more preferably from 2.5 wt % to 29 wt %, even more preferably from 3.0 wt % to 28 wt %, even more preferably from 3.5 wt % to 27 wt %, and most preferably from 3.5 wt % to 26.5 wt %.

In addition, the amount of the disintegrant can vary from 0.1 mg to 150 mg, preferably from 0.50 mg to 145 mg, more preferably from 0.75 mg to 140 mg, still more preferably from 1.00 mg to 135 mg, still more preferably from 1.25 mg to 130 mg, still more preferably from 1.50 mg to 125 mg, still more preferably from 1.75 mg to 120 mg, still more preferably from 2.00 mg to 115 mg, still more preferably from 2.25 mg to 110 mg, still more preferably from 2.50 mg to 105 mg, still more preferably from 2.75 mg to 100 mg, still more preferably from 3.00 mg to 95 mg, even more preferably from 3.25 mg to 90 mg, even more preferably from 3.50 mg to 85 mg, even more preferably from 3.75 mg to 80 mg, even more preferably from 4.00 mg to 75 mg, even more preferably from 4.25 mg to 70 mg, even more preferably 4.50 mg to 65 mg, even more preferably 4.75 mg to 60 mg, even more preferably 5.00 mg to 55 mg, even more preferably 5.50 mg to 50 mg, even more preferably 6.00 mg to 45 mg, even more preferably 6.50 mg to 42.5 mg, even more preferably 7.00 mg to 40 mg, even more preferably 7.50 mg to 40 mg, even more preferably 8.00 mg to 40 mg, even more preferably 8.50 mg to 40 mg, even more preferably 9.00 mg to 40 mg, even more preferably 9.50 mg to 40 mg, and most preferably form 10 mg to 40 mg.

Furthermore, a mass ratio of the disintegrant relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 12 m/m, preferably from 0.06 to 11.5 m/m, more preferably from 0.07 to 11 m/m, still more preferably from 0.08 to 10.5 m/m, still more preferably from 0.09 to 10 m/m, still more preferably from 0.1 to 9.5 m/m, still more preferably from 0.11 to 9 m/m, still more preferably from 0.12 to 8.5 m/m, still more preferably from 0.13 to 8 m/m, still more preferably from 0.14 to 7.5 m/m, still more preferably from 0.15 to 7 m/m, even more preferably from 0.16 to 6.5 m/m, even more preferably from 0.17 to 5.5 m/m, even more preferably from 0.18 to 5 m/m, even more preferably from 0.19 to 5 m/m, and most preferably 0.2 to 5 m/m.

The amount of the lubricant/glidant can range from 0.1 wt % to 10 wt %, preferably from, more preferably from 0.25 wt % to 9.5 wt %, still more preferably from 0.5 wt % to 9 wt %, still more preferably from 0.75 wt % to 8.5 wt %, still more preferably from 1 wt % to 8 wt %, still more preferably from 1.25 wt % to 7.5 wt %, still more preferably from 1.5 wt % to 7 wt %, and even more preferably 1.5 wt % to 6.5 wt %. Moreover, the amount of the lubricant/glidant can range from 0.01 mg to 100 mg, preferably from 0.05 mg to 95 mg, more preferably from 0.1 mg to 90 mg, still more preferably from 0.3 mg to 85 mg, still more preferably from 0.4 mg to 80 mg, still more preferably from 0.5 mg to 0.6 mg, still more preferably from 0.7 mg to 70 mg, still more preferably from 0.8 mg to 65 mg, still more preferably from 0.9 mg to 60 mg, still more preferably from 1 mg to 55 mg, still more preferably from 1.1 mg to 50 mg, still more preferably from 1.2 mg to 45 mg, still more preferably from 1.3 mg to 40 mg, still more preferably from 1.4 mg to 35 mg, still more preferably from 1.5 mg to 30 mg, still more preferably from 1.6 mg to 25 mg, still more preferably from 1.7 mg to 20 mg, even more preferably from 1.8 mg to 20 mg, even more preferably from 1.9 mg to 20 mg, even preferably from 2 mg to 20 mg, even preferably from 3 mg to 20 mg, even preferably from 4 mg to 20 mg, and most preferably even preferably from 5 mg to 20 mg.

Furthermore, a mass ratio of the lubricant/glidant relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 2 m/m, preferably from 0.06 to 1.8 m/m, more preferably from 0.07 to 1.6 m/m, 0.08 to 1.4 m/m, still more preferably from 0.09 to 1.3 m/m, and most preferably from 0.1 to 1.2 m/m.

The amount of diluent/filler/binder in the composition can range from 0 wt % to 50% wt %, preferably from 1 wt % to 47.5% wt %, more preferred from 1.5 wt % to 45% wt %, more preferred from 2 wt % to 42.5% wt %, more preferred from 2.5 to 40 wt %, more preferred from 3 wt % to 38% wt %, more preferred 3.5 wt % to 38 wt %, more preferred 4 wt % to 38 wt %, more preferred to wt %, more preferred 4.5 wt % to 38 wt %, and even more preferred 5 wt % to 38 wt %

Moreover, the amount of the diluent/filler/binder can range from 1 mg to 290 mg, preferably from 2 mg to 280 mg, more preferably from 3 mg to 270 mg, even more preferably from 4 mg to 260 mg, even more preferably from 5 mg to 250 mg, even more preferably from 6 mg to 240 mg, even more preferably from 7 mg to 230 mg, even more preferably from 8 mg to 220 mg, even more preferably from 9 mg to 210 mg, even more preferably from 10 mg to 200 mg, even more preferably from 11 mg to 190 mg, even more preferably from 12 mg to 180 mg, even more preferably from 13 mg to 170 mg, even more preferably from 14 mg to 160 mg, even more preferably from 15 mg to 150 mg, even more preferably from 16 mg to 140 mg, even more preferably from 17 mg to 130 mg, even more preferably from 18 mg to 120 mg, even more preferably from 19 mg to 110 mg, even more preferably from 19 mg to 100 mg, even more preferably from 20 mg to 90 mg, more preferably from 21 mg to 80 mg, even more preferably from 22 mg to 70 mg, even more preferably from 23 mg to 60 mg, even more preferably from 24 mg to 55 mg, and most preferably 25 mg to 50 mg.

Furthermore, a mass ratio of the diluent/filler/binder relative to the mass of (S,E)-methyl-7-(1-(2-(2-ethylbutylamino)-2-oxoethyl)-2-oxo-1,2-dihydro-pyridin enantiomer, a solvate, a hydrate or a pharmaceutically acceptable salt thereof can range from 0.01 m/m to 17.5 m/m, more preferably 0.05 m/m to 15 m/m, more preferably 0.1 m/m to 0.125 m/m, more preferably 0.15 m/m to 10 m/m, more preferably 0.175 m/m to 7.5 m/m, more preferably 0.2 m/m to 6, more preferably 0.2 m/m to 5.5, more preferably 0.2 m/m to 5 m/m.

The amount of other ingredients can range from 5 wt % to 60 wt %, preferably from 6 wt % to 57.5 wt %, more preferably 7 wt % to 55 wt %, even more preferably from 8 wt % to 52.5 wt %, even more preferably from 9 wt % to 51 wt %, and most preferably 10 wt % to 50 wt % with respect to dosage form.

In addition, the amount of other ingredients can range from 50 mg to 200 mg, preferably from 55 mg to 190 mg, more preferably from 60 mg to 180 mg, still more preferably from 65 mg to 170 mg, still more preferably from 70 mg to 160 mg, still more preferably from 75 mg to 150 mg, still more preferably from 80 mg to 140 mg, still more preferably from 90 mg to 130 mg, even more preferably from 90 mg to 120 mg, even more preferably from 90 mg to 110 mg, and most preferably from 90 mg to 100 mg.

Furthermore, a mass ratio of the capsule relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 to 30 m/m, preferably from 0.2 to 27.5 m/m, more preferably from 0.3 to 25 m/m, still more preferably from 0.35 to 22.5 m/m, even more preferably from 0.4 to 21 m/m, and most preferably from 0.45 to 20 m/m.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-enoate or an enantiomer, a solvate, a hydrate or a pharmaceutically acceptable salt thereof.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

A more preferred embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A more preferred embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A more preferred embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

A preferred embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 5 wt % to 50 wt % adipic acid.

A preferred embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A preferred embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

A preferred embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A preferred embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A preferred embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 35 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 30 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxypropyl cellulose and/or hydroxypropyl cellulose.

A preferred embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

A preferred embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxy-propyl cellulose and/or hydroxypropyl cellulose.

A preferred embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxy-propyl cellulose and/or hydroxypropyl cellulose.

A preferred embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxy-propyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxy-propyl cellulose and/or hydroxypropyl cellulose.

A preferred embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbuty-lamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

A preferred embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbuty-lamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carbox-amido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 15 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-

(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 15 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25. An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 15 wt % binder, 0.1 wt % to 35 wt % disintegrant, and 0.1 wt % to 10 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

A preferred embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 30 wt % binder, 0.1 wt % to 35 wt % disintegrant, and 0.1 wt % to 10 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 15 wt % povidone K25, 0.1 wt % to 35 wt % sodium croscarmellose, and 0.1 wt % to 10 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxy-propyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxy-propyl cellulose, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxy-propyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxy-propyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxy-propyl cellulose, and 0 wt % to 12 wt % povidone K25.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxy-propyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxy-propyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxy-propyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl- 1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide. An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

A very preferred embodiment of the invention is related to a systemic formulation for use in the prophylaxis and/or treatment of coeliac disease, wherein the systemic formulation is a capsule comprising 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30 wt %. L-hydroxypropyl cellulose, 2 wt % to 35 wt % sodium croscarmellose, and 1 wt % to 9 wt % talc or silicon dioxide and preferably 1 wt % to 9 wt % talc.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 15 wt % binder, 0.1 wt % to 35 wt % disintegrant, 0.1 wt % to 10 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, and 0 wt % to 50 wt % diluent/filler/binder.

An embodiment of the invention is related to a systemic formulation for use in the prophylaxis and/or treatment of coeliac disease comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 15 wt % povidone K25, 0.1 wt % to 35 wt % sodium croscarmellose, 0.1 wt % to 10 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxo- An embodiment of the invention is related to a systemic formulation for use in the prophylaxis and/or treatment of ethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose. An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 5 wt % to 60 wt % adipic acid, 1.00 wt % to 40 wt % L-hydroxypropyl cellulose and/or povidone K25, 2.00 wt % to 15 wt % sodium croscarmellose, and 0.10 wt % to 10 wt % talc or silicon dioxide.

A more preferred embodiment according to the invention is directed to a systemic formulation for use in the prophylaxis and/or treatment of coeliac disease comprising or consisting of 0.1 wt % to 30 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 5 wt % to 50 wt % adipic acid, 3.5 wt % to 30 wt % L-hydroxypropyl cellulose and/or povidone K25, 3.7 wt % to 15 wt % sodium croscarmellose, and 0.5 wt % to 4.00 wt % talc or silicon dioxide.

A more preferred embodiment according to the invention is directed to a systemic formulation for use in the prophylaxis and/or treatment of coeliac disease, wherein the systemic formulation is a tablet comprising or consisting of 0.1 wt % to 30 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 5 wt % to 50 wt % adipic acid, 3.5 wt % to 30 wt % L-hydroxypropyl cellulose, 3.7 wt % to 15 wt % sodium croscarmellose, and 0.5 wt % to 4.00 wt % talc.

A very preferred embodiment according to the invention is directed to a systemic formulation for use in the prophylaxis and/or treatment of coeliac disease, wherein the systemic formulation is a tablet comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30 wt % L-hydroxypropyl cellulose, 0 wt % to 30 wt % mannitol, 2 wt % to 35 wt % sodium croscarmellose, and 1 wt % to 9 wt % talc or silicon dioxide.

This systemic formulation is preferably in the form of a tablet, coated tablet, capsule, powder, or granules.

A further very preferred embodiment according to the invention is directed to a systemic formulation for use in the prophylaxis and/or treatment of coeliac disease, wherein the systemic formulation is a tablet comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 35 to 50 wt % microcrystalline cellulose, 5 wt % to 50 wt % adipic acid, 3.5 wt % to 30 wt % L-hydroxypropyl cellulose, 0.01 wt % to 30 wt % mannitol, 3.7 wt % to 15 wt % sodium croscarmellose, and 0.5 wt % to 4.00 wt % silicon dioxide.

This systemic formulation is preferably in the form of a tablet, coated tablet, capsule, powder, or granules.

A preferred embodiment of the invention is related to a systemic formulation preferably for use in the prophylaxis and/or treatment of coeliac disease comprising 0.3 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1 wt % adipic acid, 17.47 wt % L-hydroxypropyl cellulose, 7.18 wt % sodium croscarmellose, and 3 wt % talc.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0 to 50 wt % diluent/filler/binder, 0.1 wt % to 40 wt % polymeric precipitation inhibitor, 0 wt % to 15 wt % binder, 0.1 wt % to 35 wt % disintegrant, and 0.1 wt % to 10 wt % lubricant/glidant.

An embodiment of the invention is related to a systemic formulation for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0 to 50 wt % diluent/filler/binder, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation for use in the prophylaxis and/or treatment of coeliac disease comprising or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 1 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation for use in the prophylaxis and/or treatment of coeliac disease comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 1 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation for use in the prophylaxis and/or treatment of coeliac disease comprising or consisting of or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0 to 50 wt % diluent/filler/binder, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation for use in the prophylaxis and/or treatment of coeliac disease comprising or consisting of or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 3 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation for use in the prophylaxis and/or treatment of coeliac disease comprising or consisting of or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 3 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0 to 50 wt % diluent/filler/binder, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 4.5 wt % to 55 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 4.5 wt % to 55 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

Another more preferred embodiment according to the invention is directed to a systemic formulation for use in the prophylaxis and/or treatment of coeliac disease for use in the prophylaxis and/or treatment of coeliac disease, wherein the systemic formulation is a tablet comprising or consisting of 0.1 wt % to 30 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 35 wt % to 50 wt % diluent/filler/binder, 5 wt % to 50 wt % acidifier, 3.50 wt % to 30 wt % polymeric precipitation inhibitor, 0.01 wt % to 15 wt % binder, 3.70 wt % to 15 wt % disintegrant, and 0.5 wt % to 4.00 wt % lubricant/glidant.

An embodiment of the invention is related to a systemic formulation for use in the prophylaxis and/or treatment of coeliac disease comprising or consisting of or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoat or an enantiomer, a solvate, a hydrate or a pharmaceutically acceptable salt thereof, 0 to 50 wt % microcrystalline cellulose, 5 wt % to 75 wt % adipic acid, 0.1 wt % to 40 wt % L-hydroxypropyl cellulose and/or hydroxypropyl cellulose, 0 wt % to 15 wt % povidone K25, 0.1 wt % to 35 wt % sodium croscarmellose, and 0.1 wt % to 9 wt % talc or silicon dioxide.

An embodiment of the invention is related to a systemic formulation for use in the prophylaxis and/or treatment of coeliac disease for use in the prophylaxis and/or treatment of coeliac disease comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl- 1H-imidazole-5-carboxamido)-7-oxohept-2-enoat or an enantiomer, a solvate, a hydrate or a pharmaceutically acceptable salt thereof, 0 to 50 wt % microcrystalline cellulose, 1 wt % to 75 wt % adipic acid, 0.1 wt % to 40 wt % L-hydroxypropyl cellulose and/or hydroxypropyl cellulose, 0 wt % to 15 wt % povidone K25, 2 wt % to 35 wt % sodium croscarmellose, and 1 wt % to 9 wt % talc or silicon dioxide.

A more preferred embodiment according to the invention is directed to a systemic formulation for use in the prophylaxis and/or treatment of coeliac disease comprising or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 to 50 wt % microcrystalline cellulose, 1 wt % to 75 wt % adipic acid, 0.1 wt % to 40 wt % L-hydroxypropyl cellulose and/or hydroxypropyl cellulose, 0 wt % to 15 wt % povidone K25, 2 wt % to 35 wt % sodium croscarmellose, and 1 wt % to 9 wt % talc or silicon dioxide.

Another more preferred embodiment according to the invention is directed to a systemic formulation for use in the prophylaxis and/or treatment of coeliac disease for use in the prophylaxis and/or treatment of coeliac disease, wherein the systemic formulation is a tablet comprising or consisting of 0.1 wt % to 30 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 35 to 50 wt % microcrystalline cellulose, 5 wt % to 50 wt % adipic acid, 3.50 wt % to 30 wt % L-hydroxypropyl cellulose, 0.01 wt % to 15 wt % povidone K25, 3.70 wt % to 15 wt % sodium croscarmellose, and 0.5 wt % to 4.00 wt % silicon dioxide.

If the systemic formulation is disclosed as a formulation consisting of ingredients in certain amounts (weight percent, mass ratio and/or absolute mass), the rest are other ingredients, i.e. it is balanced to 100 wt % with other ingredients. The other ingredients are described above.

In the following formulation, the specific weight percent relates to the ratio of the respective compounds relative to the total amount of the listed compounds.

A preferred embodiment of the invention is related to a systemic formulation preferably for use in the prophylaxis and/or treatment of coeliac disease comprising a composition consisting of 5.21 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 9.38 wt % adipic acid, 25 wt %, L-hydroxypropyl cellulose, 3.13 wt % hydroxypropyl cellulose, 26.04 wt % sodium croscarmellose, 26.04 wt % mannitol and 5.21 wt % talc.

A preferred embodiment of the invention is related to a systemic formulation preferably for use in the prophylaxis and/or treatment of coeliac disease comprising a composition consisting of 9.09 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 16.36 wt % adipic acid, 21.82 wt %, L-hydroxypropyl cellulose, 2.73 wt % hydroxypropyl cellulose, 22.73 wt % sodium croscarmellose, 22.73 wt % mannitol and 4.55 wt % talc.

A preferred embodiment of the invention is related to a systemic formulation preferably for use in the prophylaxis and/or treatment of coeliac disease comprising a composition consisting of 3.25 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 37.34 wt % adipic acid, 16.23 wt %, L-hydroxypropyl cellulose, 8.12 wt % sodium croscarmellose, and 3.90 wt % talc.

A preferred embodiment of the invention is related to a systemic formulation preferably for use in the prophylaxis and/or treatment of coeliac disease comprising a composition consisting of 15.92 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 28.66 wt % adipic acid, 15.29 wt %, L-hydroxypropyl cellulose, 1.91 wt % hydroxypropyl cellulose, 15.92 wt % sodium croscarmellose, 15.92 wt % mannitol and 6.37 wt % talc.

A preferred embodiment of the invention is related to a systemic formulation preferably for use in the prophylaxis and/or treatment of coeliac disease comprising a composition consisting of 22.03 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 39.65 wt % adipic acid, 10.57 wt % L-hydroxypropyl cellulose, 1.32 wt % hydroxypropyl cellulose, 11.01 wt % sodium croscarmellose, 11.01 wt % mannitol and 4.41 wt % talc.

A preferred embodiment of the invention is related to a systemic formulation preferably for use in the prophylaxis and/or treatment of coeliac disease comprising a composition consisting of 18.80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 33.83 wt % adipic acid, 3.76 wt % L-hydroxypropyl cellulose, 3.76 wt % sodium croscarmellose, and 3.76 wt % talc.

A preferred embodiment of the invention is related to a systemic formulation preferably for use in the prophylaxis and/or treatment of coeliac disease comprising a composition consisting of 27.03 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 48.65 wt % adipic acid, 6.49 wt % L-hydroxypropyl cellulose, 1.62 wt % hydroxypropyl cellulose, 6.76 wt % sodium croscarmellose, 6.76 wt % mannitol and 2.7 wt % talc.

A preferred embodiment of the invention is related to a systemic formulation preferably for use in the prophylaxis and/or treatment of coeliac disease comprising a composition consisting of 23.20 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 41.76 wt % adipic acid, 4.64 wt % L-hydroxypropyl cellulose, 4.64 wt % sodium croscarmellose, and 3.48 wt % talc.

A preferred embodiment of the invention is related to a systemic formulation preferably for use in the prophylaxis and/or treatment of coeliac disease comprising a composition consisting of 26.46 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 47.62 wt % adipic acid, 5.29 wt % L-hydroxypropyl cellulose, 5.29 wt % sodium croscarmellose, and 2.65 wt % talc.

A preferred embodiment of the invention is related to a systemic formulation preferably for use in the prophylaxis and/or treatment of coeliac disease comprising or consisting of 7.6 wt % (S,E)-methyl-7-(1-(2-(2-ethylbutylamino)-2-oxoethyl)-2-oxo-1,2-dihydro-pyridin-3-ylamino)-6-(1- methyl-1H-imidazole-5-carboxamido)-7-oxohept-2-enoate, 13.7 wt % adipic acid, 18.3 wt % L-hydroxypropyl cellulose, 8.4 wt % povidone K25, 13.7 wt % sodium croscarmellose, 36.6 wt % microcrystalline cellulose and 1.5 wt % silicon dioxide.

An embodiment of the invention is related to a systemic formulation for use in the prophylaxis and/or treatment of coeliac disease comprising or consisting of at least 0.01 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose.

An embodiment of the invention is related to a systemic formulation for use in the prophylaxis and/or treatment of coeliac disease comprising or consisting of at least 0.1 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose.

A preferred embodiment of the invention is related to a systemic formulation for use in the prophylaxis and/or treatment of coeliac disease comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose and/or hydroxypropyl cellulose and up to 100 mg povidone K25.

An embodiment of the invention is related to a systemic formulation for use in the prophylaxis and/or treatment of coeliac disease comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 5 mg to 500 mg adipic acid, 1 mg to 100 mg L-hydroxypropyl cellulose and hydroxypropyl cellulose, up to 100 mg povidone K25, 1 mg to 100 mg sodium croscarmellose, and 1 mg to 50 mg talc or silicon dioxide.

An embodiment of the invention is related to a systemic formulation preferably for use in the prophylaxis and/or treatment of coeliac disease comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 360 mg adipic acid, 1 mg to 40 mg L-hydroxypropyl cellulose, 10 mg to 40 mg sodium croscarmellose, and 1 mg to 20 mg talc or silicon dioxide.

An embodiment of the invention is related to a systemic formulation preferably for use in the prophylaxis and/or treatment of coeliac disease comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 9 mg to 360 mg adipic acid, 10 mg to 40 mg L-hydroxypropyl cellulose, 10 mg to 40 mg sodium croscarmellose, and 1 mg to 20 mg talc or silicon dioxide.

A preferred embodiment of the invention is related to a systemic formulation preferably for use in the prophylaxis and/or treatment of coeliac disease comprising 0.5 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 mg adipic acid, 0.2 mg L-hydroxypropyl cellulose, 2.5 mg sodium croscarmellose, and 0.2 mg talc.

A preferred embodiment of the invention is related to a systemic formulation for use in the prophylaxis and/or treatment of coeliac disease comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose and/or hydroxypropyl cellulose and up to 100 mg povidone K25.

An embodiment of the invention is related to a systemic formulation for use in the prophylaxis and/or treatment of coeliac disease comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 5 mg to 500 mg adipic acid, 1 mg to 100 mg L-hydroxypropyl cellulose and hydroxypropyl cellulose, up to 100 mg povidone K25, 1 mg to 100 mg sodium croscarmellose, and 1 mg to 50 mg talc or silicon dioxide.

An embodiment of the invention is related to a systemic formulation preferably for use in the prophylaxis and/or treatment of coeliac disease comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 360 mg adipic acid, 1 mg to 40 mg L-hydroxypropyl cellulose, 10 mg to 40 mg sodium croscarmellose, and 1 mg to 20 mg talc or silicon dioxide.

An embodiment of the invention is related to a systemic formulation preferably for use in the prophylaxis and/or treatment of coeliac disease comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 9 mg to 360 mg adipic acid, 10 mg to 40 mg L-hydroxypropyl cellulose, 10 mg to 40 mg sodium croscarmellose, and 1 mg to 20 mg talc or silicon dioxide.

A preferred embodiment of the invention is related to a systemic formulation preferably for use in the prophylaxis and/or treatment of coeliac disease comprising 1 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 mg adipic acid, 0.2 mg L-hydroxypropyl cellulose, 2.5 mg sodium croscarmellose, and 0.2 mg talc.

A preferred embodiment of the invention is related to a systemic formulation preferably for use in the prophylaxis and/or treatment of coeliac disease comprising 2 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3.6 mg adipic acid, 10 mg L-hydroxypropyl cellulose, 5 mg sodium croscarmellose, and 2.4 mg talc.

A preferred embodiment of the invention is related to a systemic formulation preferably for use in the prophylaxis and/or treatment of coeliac disease comprising 5 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5- carboxamido)-7-oxohept-2-enoate, 9 mg adipic acid, 24 mg L-hydroxypropyl cellulose, 3 mg hydroxypropyl cellulose, 25 mg sodium croscarmellose, 25 mg mannitol and 5 mg talc.

A preferred embodiment of the invention is related to a systemic formulation preferably for use in the prophylaxis and/or treatment of coeliac disease comprising 5 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 9 mg adipic acid, 25 mg L-hydroxypropyl cellulose, 12.5 mg sodium croscarmellose, and 6 mg talc.

A preferred embodiment of the invention is related to a systemic formulation preferably for use in the prophylaxis and/or treatment of coeliac disease comprising 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 16.36 mg adipic acid, 24 mg L-hydroxypropyl cellulose, 3 mg hydroxypropyl cellulose, 25 mg sodium croscarmellose, 25 mg mannitol and 5 mg talc.

A preferred embodiment of the invention is related to a systemic formulation preferably for use in the prophylaxis and/or treatment of coeliac disease comprising 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 115 mg adipic acid, 50 mg L-hydroxypropyl cellulose, 25 mg sodium croscarmellose, and 12 mg talc.

A preferred embodiment of the invention is related to a systemic formulation preferably for use in the prophylaxis and/or treatment of coeliac disease comprising 25 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 45 mg adipic acid, 24 mg L-hydroxypropyl cellulose, 3 mg hydroxypropyl cellulose, 25 mg sodium croscarmellose, 25 mg mannitol and 10 mg talc.

A preferred embodiment of the invention is related to a systemic formulation preferably for use in the prophylaxis and/or treatment of coeliac disease comprising 50 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 90 mg adipic acid, 24 mg L-hydroxypropyl cellulose, 3 mg hydroxypropyl cellulose, 25 mg sodium croscarmellose, 25 mg mannitol and 10 mg talc.

A preferred embodiment of the invention is related to a systemic formulation preferably for use in the prophylaxis and/or treatment of coeliac disease comprising 50 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 90 mg adipic acid, 10 mg L-hydroxypropyl cellulose, 10 mg sodium croscarmellose, and 10 mg talc.

A preferred embodiment of the invention is related to a systemic formulation preferably for use in the prophylaxis and/or treatment of coeliac disease comprising 100 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 180 mg adipic acid, mg 24 mg L-hydroxypropyl cellulose, 6 mg hydroxypropyl cellulose, 25 mg sodium croscarmellose, 25 mg mannitol and 10 mg talc.

A preferred embodiment of the invention is related to a systemic formulation preferably for use in the prophylaxis and/or treatment of coeliac disease comprising 100 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 180 mg adipic acid, 20 mg L-hydroxypropyl cellulose, 20 mg sodium croscarmellose, and 15 mg talc.

A preferred embodiment of the invention is related to a systemic formulation preferably for use in the prophylaxis and/or treatment of coeliac disease comprising 200 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 360 mg adipic acid, 40 mg L-hydroxypropyl cellulose, 40 mg sodium croscarmellose, and 20 mg talc.

A preferred embodiment of the invention is related to a systemic formulation preferably for use in the prophylaxis and/or treatment of coeliac disease comprising 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 48 mg microcrystalline cellulose, 18 mg adipic acid, 24 mg L-hydroxypropyl cellulose, 11 mg povidone K25, 18 mg sodium croscarmellose, and 2 mg silicon dioxide.

Another preferred embodiment of the invention is related to a systemic formulation preferably for use in the prophylaxis and/or treatment of coeliac disease comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 5 mg to 500 mg adipic acid, 1 mg to 100 mg L-hydroxypropyl cellulose, 1 mg to 100 mg sodium croscarmellose, 1 mg to 50 mg talc, 50 mg to 200 mg gelatine, and 0.5 mg to 5 mg titanium dioxide.

A preferred embodiment of the invention is related to a systemic formulation preferably for use in the prophylaxis and/or treatment of coeliac disease comprising 5 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 9 mg adipic acid, 24 mg L-hydroxypropyl cellulose, 3 mg hydroxypropyl cellulose, 25 mg sodium croscarmellose, 25 mg mannitol, 5 mg talc, 94.08 mg gelatine, and 1.92 mg titanium dioxide.

A preferred embodiment of the invention is related to a systemic formulation preferably for use in the prophylaxis and/or treatment of coeliac disease comprising 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 16.36 mg adipic acid, 24 mg L-hydroxypropyl cellulose, 3 mg hydroxypropyl cellulose, 25 mg sodium croscarmellose, 25 mg mannitol, 5 mg talc, 94.08 mg gelatine, and 1.92 mg titanium dioxide.

A further preferred embodiment of the invention is related to a systemic formulation preferably for use in the prophylaxis and/or treatment of coeliac disease comprising or consisting of 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 115 mg adipic acid, 50 mg L-hydroxypropyl cellulose, 25 mg sodium croscarmellose, 12 mg talc, 94.08 mg gelatine, and 1.92 mg titanium dioxide.

A preferred embodiment of the invention is related to a systemic formulation preferably for use in the prophylaxis and/or treatment of coeliac disease comprising 25 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 45 mg adipic acid, 24 mg L-hydroxypropyl cellulose, 3 mg hydroxypropyl cellulose, 25 mg sodium croscarmellose, 25 mg mannitol, 10 mg talc, 94.08 mg gelatine, and 1.92 mg titanium dioxide.

A preferred embodiment of the invention is related to a systemic formulation preferably for use in the prophylaxis and/or treatment of coeliac disease comprising 50 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 90 mg adipic acid, 24 mg L-hydroxypropyl cellulose, 3 mg hydroxypropyl cellulose, 25 mg sodium croscarmellose, 25 mg mannitol, 10 mg talc, 94.08 mg gelatine, and 1.92 mg titanium dioxide.

A further preferred embodiment of the invention is related to a systemic formulation preferably for use in the prophylaxis and/or treatment of coeliac disease comprising or consisting of 50 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 90 mg adipic acid, 10 mg L-hydroxypropyl cellulose, 10 mg sodium croscarmellose, 10 mg talc, 94.08 mg gelatine, and 1.92 mg titanium dioxide.

A preferred embodiment of the invention is related to a systemic formulation preferably for use in the prophylaxis and/or treatment of coeliac disease comprising 100 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 180 mg adipic acid, mg 24 mg L-hydroxypropyl cellulose (low substituted), 6 mg hydroxypropyl cellulose, 25 mg sodium croscarmellose, 25 mg mannitol, 10 mg talc, 94.08 mg gelatine, and 1.92 mg titanium dioxide. A further preferred embodiment of the invention is related to a systemic formulation preferably for use in the prophylaxis and/or treatment of coeliac disease comprising or consisting of: 100 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 180 mg adipic acid, 20 mg L-hydroxypropyl cellulose, 20 mg sodium croscarmellose, 15 mg talc, 94.08 mg gelatine, and 1.92 mg titanium dioxide.

A preferred embodiment of the invention is related to a systemic formulation preferably for use in the prophylaxis and/or treatment of coeliac disease comprising or consisting of 200 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 360 mg adipic acid, 40 mg L-hydroxypropyl cellulose, 40 mg sodium croscarmellose, 20 mg talc, 94.08 mg gelatine and 1.92 mg titanium dioxide.

An embodiment of the invention is related to a systemic formulation for use in the prophylaxis and/or treatment of coeliac disease for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 15 to 1 m/m acidifier, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 11.5 to 1.5 m/m acidifier, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 11.5 to 1.8 m/m acidifier, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, 0.1 to 7 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, 0.2 to 5 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.2 to 5 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, 0.1 to 7 m/m polymeric precipitation inhibitor, 0 to 2 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 2 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 2 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, 0.1 to 7 m/m polymeric precipitation inhibitor, 0 to 5 m/m binder, 0.1 to 7 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 5 m/m binder, 0.1 to 7 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 5 m/m binder, 0.1 to 7 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, 0.1 to 7 m/m polymeric precipitation inhibitor, 0 to 5 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 5 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 5 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m acidifier, 0.1 to 7 m/m polymeric precipitation inhibitor, 0 to 5 m/m binder, 0.1 to 7 m/m disintegrant, 0.05 to 2 m/m lubricant/glidant, 0 to 5 m/m diluent/filler/binder, and 0 m/m to 25 m/m other ingredients, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 2 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 2 m/m binder, 0.2 to 5 m/m disintegrant, 0.05 to 2 m/m lubricant/glidant, and 0 to 5 m/m diluent/filler/binder, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 2 m/m binder, 0.2 to 5 m/m disintegrant, 0.05 to 2 m/m lubricant/glidant, 0 to 5 m/m diluent/filler/binder, and 0 m/m to 19.5 m/m other ingredients, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

A particularly preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 11.5 to 1.5 m/m binder, 0.2 to 5 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

Another preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m adipic acid, and 0.1 to 7 m/m L-hydroxypropyl cellulose and/or hydroxypropyl cellulose, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

Another particularly preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m adipic acid, and 0.2 to 5 m/m L-hydroxypropyl cellulose and/or hydroxypropyl cellulose, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

Another preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 15 to 1 m/m adipic acid, 0.1 to 7 m/m L-hydroxypropyl cellulose and/or hydroxypropyl cellulose, 0 to 2 m/m povidone K25, 0.2 to 5 m/m sodium croscarmellose, and 0.05 to 2 m/m talc or silicon dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

Another particularly preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m adipic acid, 0.2 to 5 m/m L-hydroxypropyl cellulose and/or hydroxypropyl cellulose, 0 to 1.5 m/m povidone K25, 0.2 to 5 m/m sodium croscarmellose, and 0.1 to 1.2 m/m talc or silicon dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 4.8 m/m L-hydroxypropyl cellulose, 0.6 m/m hydroxypropyl cellulose, 5 m/m sodium croscarmellose, 5 m/m mannitol and 1 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 2.4 m/m L-hydroxypropyl cellulose, 0.3 m/m hydroxypropyl cellulose, 2.5 m/m sodium croscarmellose, 2.5 m/m mannitol and 0.5 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 11.5 m/m adipic acid, 5 m/m L-hydroxypropyl cellulose, 2.5 m/m sodium croscarmellose, and 1.2 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 0.96 m/m L-hydroxypropyl cellulose, 0.12 m/m hydroxypropyl cellulose, 1 m/m sodium croscarmellose, 1 m/m mannitol and 0.4 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 0.48 m/m L-hydroxypropyl cellulose, 0.06 m/m hydroxypropyl cellulose, 0.5 m/m sodium croscarmellose, 0.5 m/m mannitol and 0.2 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 5 m/m L-hydroxypropyl cellulose, 0.2 m/m sodium croscarmellose, and 0.2 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 0.24 m/m L-hydroxypropyl cellulose, 0.06 m/m hydroxypropyl cellulose, 0.25 m/m sodium croscarmellose, 0.25 m/m mannitol and 0.1 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 5 m/m L-hydroxypropyl cellulose, 0.2 m/m sodium croscarmellose, and 0.15 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 5 m/m L-hydroxypropyl cellulose, 0.2 m/m sodium croscarmellose, and 0.10 m/m talc, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 4.8 m/m microcrystalline cellulose, 1.8 m/m adipic acid, 2.4 m/m L-hydroxypropyl cellulose, 1.1 m/m povidone K25, 1.8 m/m sodium croscarmellose, and 0.15 m/m silicon dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 11.5 m/m adipic acid, 5 m/m L-hydroxypropyl cellulose, 2.5 m/m sodium croscarmellose, 1.2 m/m talc, 9,408 m/m gelatine and 0.192 m/m titanium dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 5 m/m L-hydroxypropyl cellulose, 0.2 m/m sodium croscarmellose, 0.2 m/m talc, 1.88 m/m gelatine and 0.038 m/m titanium dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 5 m/m L-hydroxypropyl cellulose, 0.2 m/m sodium croscarmellose, 0.15 m/m talc, 0.94 m/m gelatine and 0.019 m/m titanium dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

A preferred embodiment of the invention is related to a systemic formulation preferably for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1.8 m/m adipic acid, 5 m/m L-hydroxypropyl cellulose, 0.2 m/m sodium croscarmellose, 0.10 m/m talc, 0.47 m/m gelatine and 0.010 m/m titanium dioxide, wherein m/m (mass ratio) of said compounds is calculated relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate. A mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 11.5 to 1 m/m, and a mass ratio of the binder/polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 0.2 to 5 m/m is preferred.

More preferred is a mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 11.5 to 1.8 m/m, and a mass ratio of the binder/polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 0.2 to 5 m/m.

A mass ratio between the acidifier and the polymeric precipitation inhibitor can vary from 0.01 m/m to 20 m/m, preferably from 0.02 m/m to 15 m/m, more preferably from 0.03 m/m to 12.5 m/m, even more preferably from 0.04 m/m to 10 m/m, even more preferably from 0.05 m/m, even more preferably from 0.06 m/m to 9 m/m, even more preferably from 0.07 m/m to 8 m/m, even more preferably from 0.08 m/m to 7 m/m, even more preferably from 0.09 m/m to 6 m/m, even more preferably from 0.1 m/m to 5 m/m, even more preferably from 0.1 m/m to 4 m/m, and most preferably from 0.1 m/m to 3 m/m, wherein the mass ration is calculated relative to the mass of the acidifier in the formulation.

A preferred embodiment of the invention is related to a systemic formulation comprising or consisting of (S,E)-methyl-7-(1-(2-(2-ethylbutylamino)-2-oxoethyl)-2-oxo-1,2- dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, acidifier, and polymeric precipitation inhibitor, wherein the mass ratio between the solution stabilizer and the acidifier ranges from 0.01 to 6 m/m, and wherein m/m (mass ratio) of said compounds is calculated relative to the mass of the acidifier.

Preferably, the formulation according to the invention is not included in a pump which is implantable. The administration by an osmotic pump is not applicable to human.

A preferred embodiment of the invention is related to a systemic formulation for use in the prophylaxis and/or treatment of coeliac disease comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, acidifier, and polymeric precipitation inhibitor, wherein the mass ratio between the acidifier and the polymeric precipitation inhibitor ranges from 0.05 to 3.5 m/m, and wherein m/m (mass ratio) of said compounds is calculated relative to the mass of the binder/polymeric precipitation inhibitor.

Preferably, the formulation according to the invention is not included in a pump which is implantable. The administration by an osmotic pump is not applicable to human.

Preferably, (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is absorbed in the duodenum with a maximal concentration in the plasma or tissue (Cmax-value) of 0.2 ng/mL to 2000 ng/mL, and wherein the Cmax-value is measured in plasma samples by liquid chromatography coupled with mass spectrometry.

The inhibitory effect is dependent from the maximal plasma or tissue concentration (cmax-value).

Another aspect of the invention is directed to a formulation according to the invention for use in the prophylaxis and/or treatment of coeliac disease in mammal preferably in human.

Another aspect of the invention is directed to a method for preparation of a formulation according to the invention comprising the step:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

The amount of (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof provided in step A-1) is mentioned above.

Thus, an embodiment of the invention is directed to a method for preparation of a formulation according to the invention comprising the step:

A-1) Providing 1 mg to 500 g (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

Thus, an embodiment of the invention is directed to a method for preparation of a formulation according to the invention comprising the step:

A-1) Providing 1 mg to 500 g (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

Another embodiment of the invention is directed to a method for preparation of a formulation according to the invention comprising the step:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

It is apparent that the amount of the drug can also be substituted by another amount as mentioned above.

In step A-2), at least one excipient, as described herein, is added. Preferably, at least one excipient is a polymeric precipitation inhibitor preferably L-hydroxypropyl cellulose, a disintegrant or a diluent/filler/binder.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2) adding at least one excipient.

In a step A-2'), the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor preferably L-hydroxypropyl cellulose and a disintegrant preferably sodium croscarmellose are sieved in a dry state preferably separately.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, a polymeric precipitation inhibitor and a disintegrant in a dry state, preferably separately.

The amount of the disintegrant, polymeric precipitation inhibitor and disintegrant in step A-2') is mentioned above.

Thus, an embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg polymeric precipitation inhibitor and 10 mg to 40 mg disintegrant in a dry state, preferably separately.

A preferred embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg L-hydroxypropyl cellulose and 10 mg to 40 mg sodium croscarmellose in a dry state, preferably separately.

Another preferred embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % polymeric precipitation inhibitor and 2 wt % to 40 wt % disintegrant in a dry state, preferably separately.

Another more preferred embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % L-hydroxypropyl cellulose and mannitol and 2 wt % to 40 wt % sodium croscarmellose in a dry state, preferably separately.

It is apparent that the amount of the excipients and the drug can also be substitute by another amount as mentioned above.

In a step A-3), a solvent can be added which leads to a particle agglomeration and the formation of the granule structure. Preferably, the solvent is ethanol.

Thus, an embodiment according to the invention is related to a method for preparation of a formulation according to the invention comprising the steps:

A-1) Providing c(S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, A-2) adding at least one excipient, and A-3) adding a solvent which leads to a particle agglomeration and the formation of the granule structure.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, and A-3) adding a solvent which leads to a particle agglomeration and the formation of the granule structure.

In a step A-4), the granule mass can be sieved in a wet state preferably the granule mass of step A-3).

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granule structure, and A-4) sieving the granule mass of step A-3) in a wet state.

In a step A-5), a granule mass in a wet state is dried, wherein dry granules are received.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state, and A-5) drying the granule mass in a wet state.

In a step B-1), an excipient preferably adipic acid and/or talc can be added to the dry granule, and mixed preferably in a dry mixer forming a powder mixture.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and B-1) adding at least one excipient.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, A-2) adding at least one excipient, and A-3) adding a solvent which leads to a particle agglomeration and the formation of the granule structure.

B-1) adding at least one excipient.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the compound (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state, A-5) drying the granule mass in a wet state, and B-1) adding at least one excipient such as an acidifier preferably adipic acid and/or a lubricant/glidant preferably talc or silicon dioxide to the dry granule.

Thus, an embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the compound (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg polymeric precipitation inhibitor and 10 mg to 40 mg disintegrant in a dry state, A-3) adding a solvent which leads to a particle agglomeration and the formation of the granulate structure, A-4) sieving the granulate mass of step A-3) in a wet state, A-5) drying the granule mass in a wet state, and B-1) adding 10 to 360 mg acidifier and/or 1 mg to 20 mg lubricant/glidant preferably talc or silicon dioxide to the dry granule.

Thus, an embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % polymeric precipitation inhibitor and 2 wt % to 40 wt % disintegrant in a dry state, A-3) adding a solvent which leads to a particle agglomeration and the formation of the granulate structure, A-4) sieving the granulate mass of step A-3) in a wet state, A-5) drying the granule mass in a wet state, and B-1) adding 5 wt % to 60 wt % acidifier and/or 0.1 wt % to 10 wt % lubricant/glidant preferably talc or silicon dioxide to the dry granule.

A preferred embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg L-hydroxypropyl cellulose and mannitol and 10 mg to 40 mg sodium croscarmellose are sieved in a dry state preferably separately.

A-3) adding a solvent which leads to a particle agglomeration and the formation of the granulate structure, A-4) sieving the granulate mass of step A-3) in a wet state, A-5) drying the granule mass in a wet state, and B-1) adding 10 to 360 mg adipic acid and 1 mg to 20 mg talc or silicon dioxide to the dry granule.

A further more preferred embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % L-hydroxypropyl cellulose and mannitol and 2 wt % to 40 wt % sodium croscarmellose are sieved in a dry state preferably separately.

A-3) adding a solvent which leads to a particle agglomeration and the formation of the granulate structure, A-4) sieving the granulate mass of step A-3) in a wet state, A-5) drying the granule mass in a wet state, and B-1) adding 5 wt % to 60 wt % adipic acid and 0.1 wt % to 10 wt % talc or silicon dioxide to the dry granule.

In a step B-1'), the excipient acidifier and/or lubricant/glidant preferably can be sieved preferably separately if two excipients are sieved.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the compound methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state, A-5) drying the granule mass in a wet state, B-1') sieving an acidifier and a lubricant/glidant such as talc or silicon dioxide, and B-1) adding the sieved acidifier and lubricant/glidant to the dry granulate.

A preferred embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg polymeric precipitation inhibitor and 10 mg to 40 mg disintegrant in a dry state, A-3) adding a solvent which leads to a particle agglomeration and the formation of the granulate structure, A-4) sieving the granulate mass of step A-3) in a wet state, A-5) drying the granule mass in a wet state, B-1') sieving 10 to 360 mg acidifier and 1 mg to 20 mg lubricant/glidant such as talc or silicon dioxide, and B-1) adding the sieved acidifier and lubricant/glidant to the dry granulate.

Another preferred embodiment according to the invention is related to a method for preparation of a formulation according to the invention comprising the steps:

A-1) Providing compound 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 0.1 wt % to 40 wt % polymeric precipitation inhibitor, 0.1 wt % to 30 wt % binder and 2 wt % to 40 wt % disintegrant in a dry state, A-3) adding a solvent which leads to a particle agglomeration and the formation of the granulate structure, A-4) sieving the granulate mass of step A-3) in a wet state, A-5) drying the granule mass in a wet state, B-1') sieving 5 wt % to 60 wt % acidifier and 0.1 wt % to 10 wt % lubricant/glidant such as talc or silicon dioxide, and B-1) adding the sieved acidifier and lubricant/glidant to the dry granulate.

In a step C-1), the formulation in different dosage forms can be obtained by filling the powder mixture of step B-1) in hard gelatine capsule or by pressing the powder mixture or granule to a tablet. The powder mixture or granules are already dosage forms. In step, C-1), also a solution suitable for a parenteral administration e.g. intravenous can be achieved if a solvent is added in step B-1) as an excipient.

Also a formulation for the parenteral administration in solid form which is used for the preparation of solution before the administration is conceivable.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, B-1) adding an excipient, and C-1) obtaining the systemic formulation.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor, a binder and a disintegrant in a dry state, A-3) adding a solvent which leads to a particle agglomeration and the formation of the granulate structure, A-4) sieving the granulate mass of step A-3) in a wet state A-5) drying the granule mass in a wet state, B-1) adding adipic acid and talc to the dry granulate, and C-1) obtaining the systemic formulation by filling the powder mixture of step B-1) in hard gelatine capsule or by pressing the granule or powder mixture to a tablet.

Abbreviations: VH:CrD=villus height-to-crypt depth ratio.

Note: Only patients who had evaluable biopsy results at both time points are included.

Figure 8:
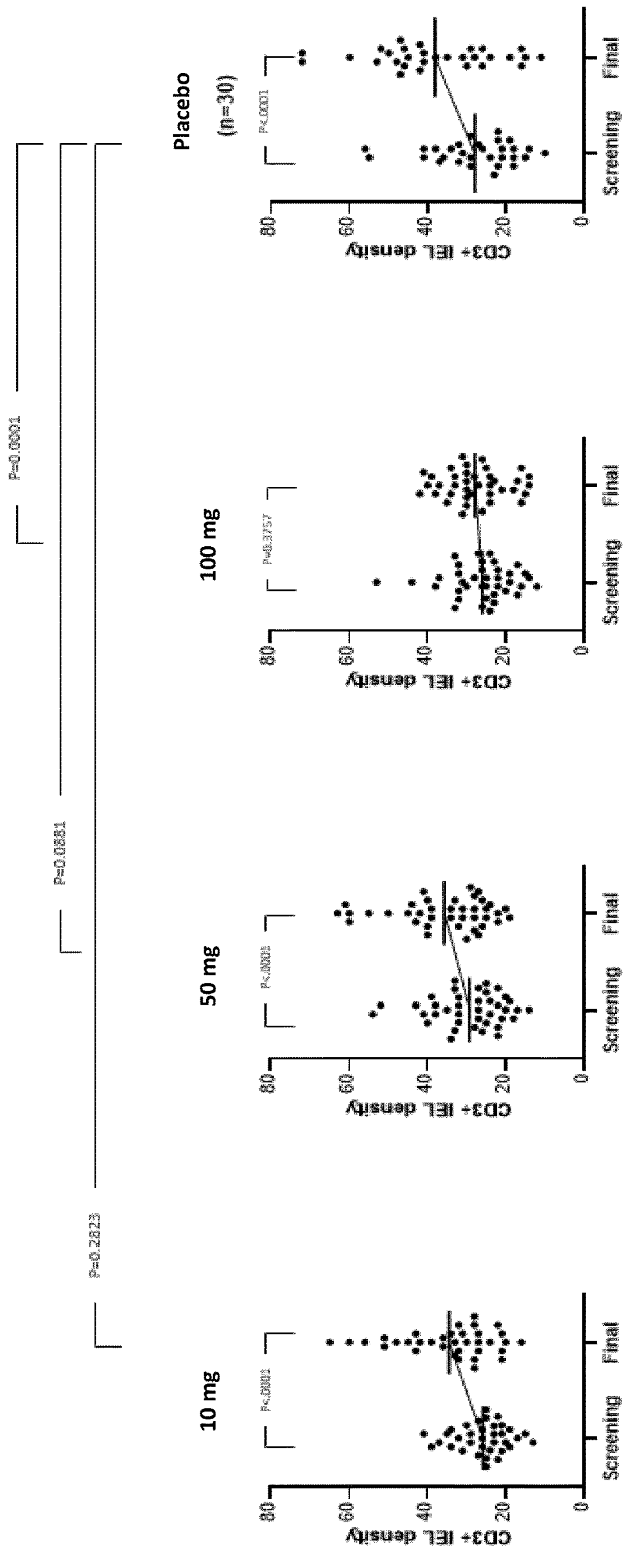

FIG. 8 shows individual patient's intraepithelia lymphocyte density.

Abbreviations: IEL=intraepithelia lymphocyte.

Note: Only patients who had evaluable biopsy results at both time points are displayed.

Figure 9:
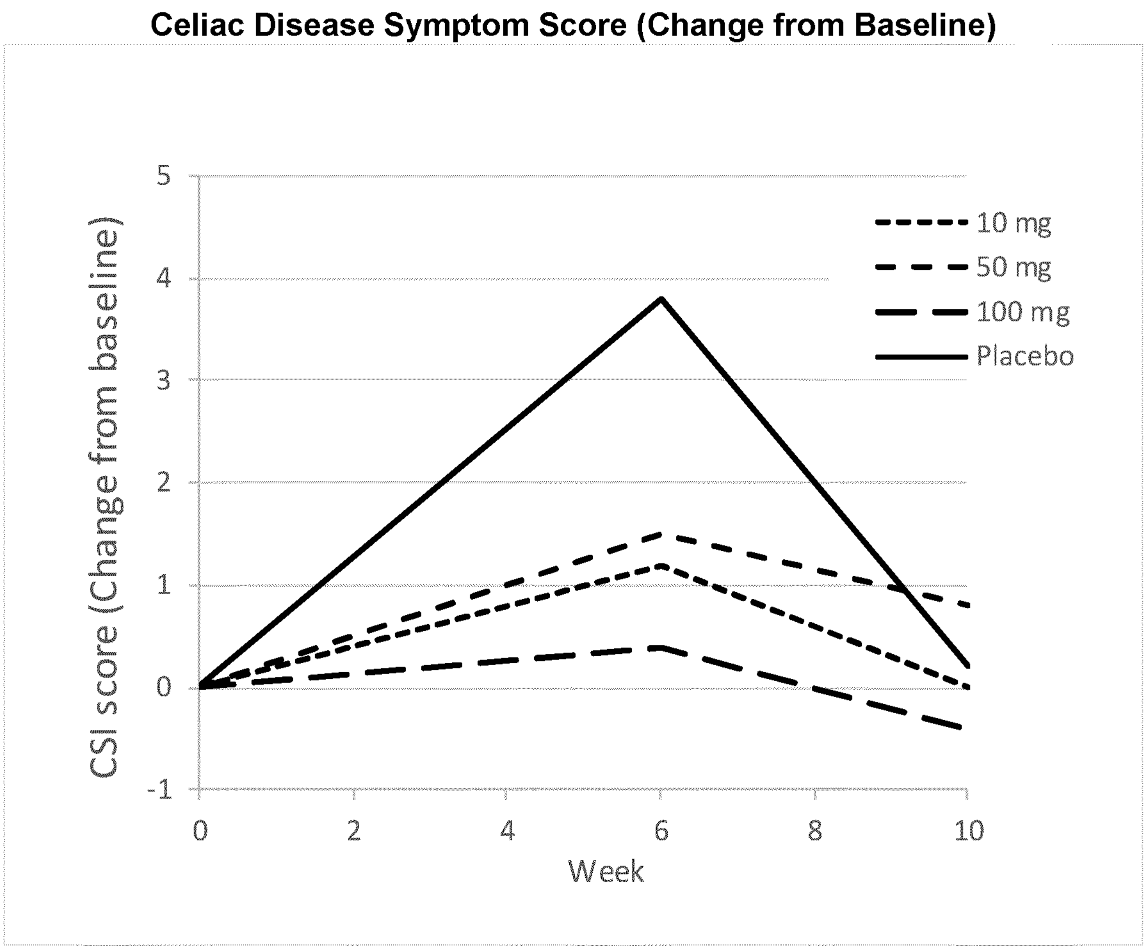

FIG. 9 shows mean (standard error [SE]) celiac system index (CSI) score.

Figure 10:
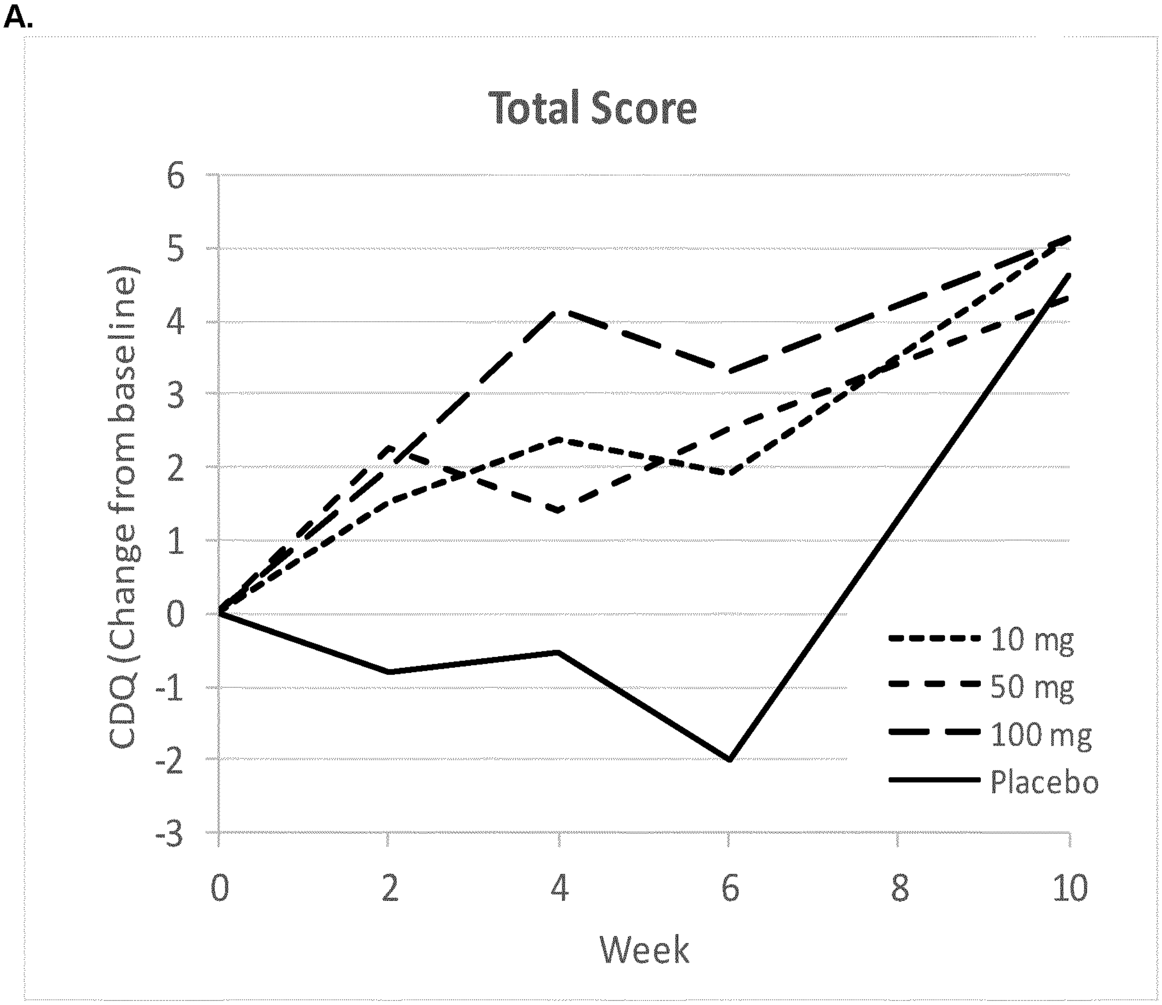
Figure 10:
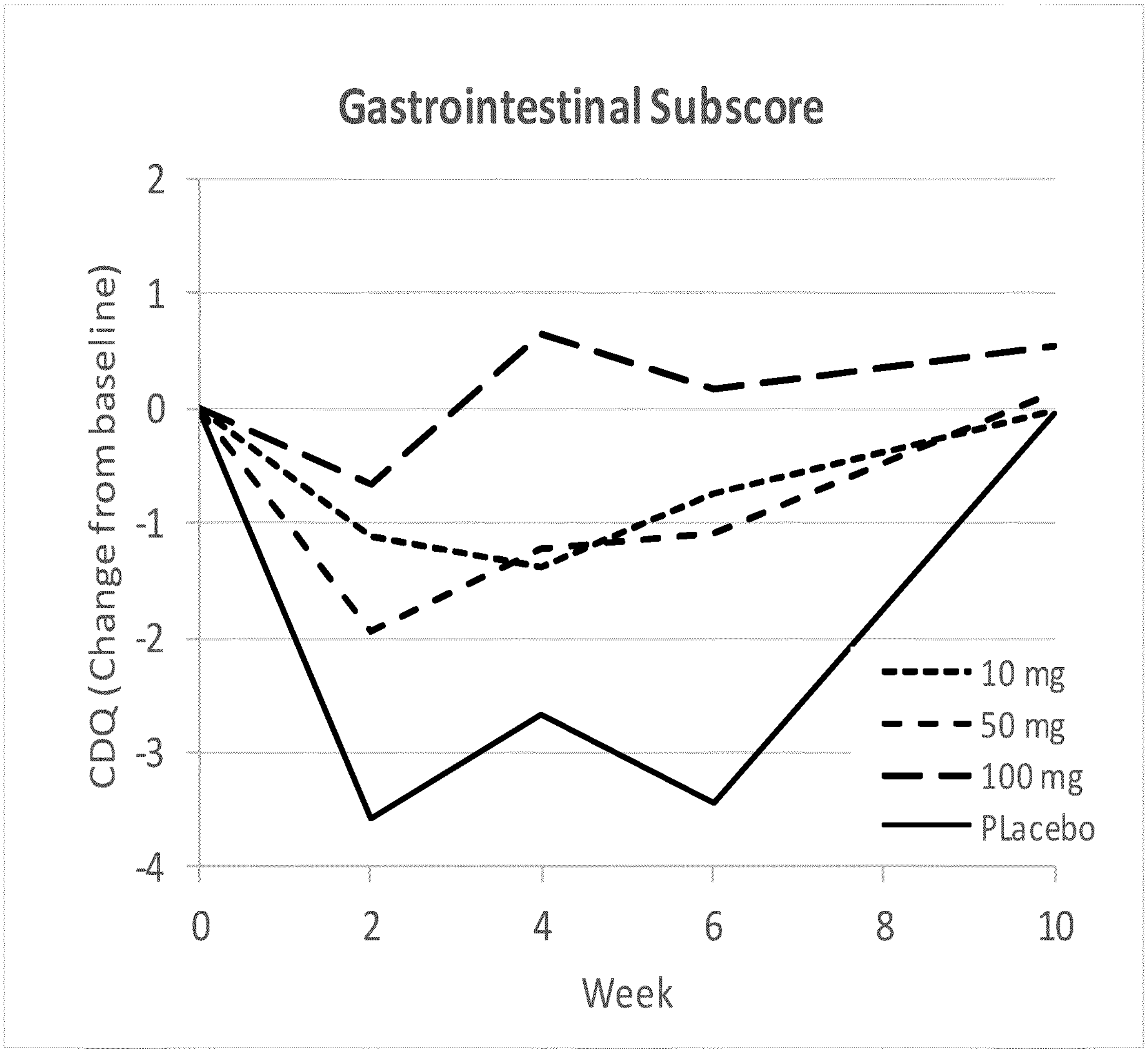

FIG. 10 A) shows mean ([SE]) celiac disease questionnaire (CDQ) total score ( ); B) shows mean ([SE]) celiac disease questionnaire (CDQ) gastrointestinal symptom subscore.

EXAMPLES

Example 1

Preparation of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (Compound of Formula (I))

Example 1.1 Preparation of 6-amino-hept-2-en-dicarboxyl acid Derivatives

(S)-1-tert-Butyl 5-methyl 2-(tert-butoxycarbonylamino)pentanedioate

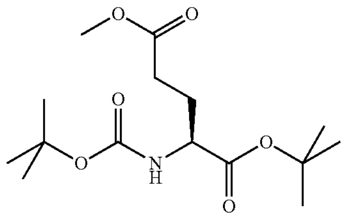

Molecular formula: C15H27NO6
Molecular weight: 317.38

12.0 g of Boc-Glu-OtBu (39.6 mmol) are dissolved in 200 mL of DMF. Under argon atmosphere, 7.09 g of cesium carbonate (21.8 mmol, 0.55 eq.) are added and the resulting suspension is stirred for 1 hour at RT. After this time, 2.47 mL of methyl iodide (39.6 mmol) are added and stirred at RT overnight. The solvent is removed in vacuo and the obtained residue is taken up in 400 mL of ethyl acetate. The undissolved solid is filtered and the filtrate is washed with respectively 75 mL of 10% citric acid, 10% $NaHCO_3$ solution and brine 3 times. After drying of the organic phase over $Na_2SO_4$ the solvent is removed in vacuo. The product is obtained as yellow oil. The product can be used without further purification in the following reaction.

Yield: 13.4 g, >100%

ESI-MS: 340.2 $[M+Na]^+$

(S)-1-tert-Butyl 5-methyl 2-(bis(tert-butoxycarbonyl)amino)pentanedioate

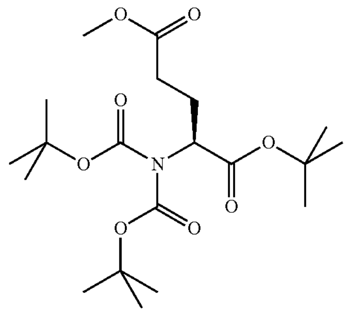

Molecular formula: C20H35NO8
Molecular weight: 417.49

13.4 g of Boc-Glu(OMe)-OtBu (~39.6 mmol) are dissolved in 30 mL of acetonitrile and treated with 986 mg of DMAP (7.91 mmol, 0.2 eq). Under nitrogen atmosphere a solution of 17.6 g of di-tert-butylbicarbonate (77.1 mmol, 2 eq) in 100 mL of acetonitrile is added. After stirring overnight, the solvent is removed in vacuo and the obtained crude product is purified by chromatography on silica gel (column: 31*6.0 cm, petroleum ether/ethyl acetate 9:1)

Column chromatography: collected in 250 mL fractions, product: fractions 6-13

TLC control: petroleum ether/ethyl acetate 8:2, $R_f$=0.70

Yield: 13.7 g, 32.8 mmol, 83%

ESI-MS: 440.3 $[M+Na]^+$

(S)-tert-Butyl 2-(bis(tert-butoxycarbonyl)amino)-5-oxopentanoate

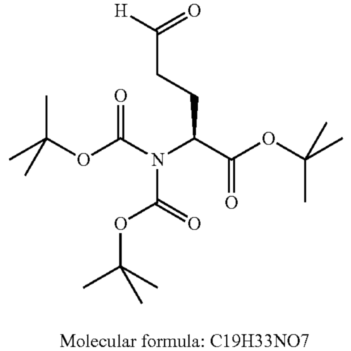

Molecular formula: C19H33NO7
Molecular weight: 387.47

13.7 g of $Boc_2$-Glu(OMe)-OtBu (32.8 mmol) are dissolved in 200 mL of absolute diethylether and cooled to −78° C. under argon atmosphere. At this temperature 36.1 mL (36.1 mmol, 1.1 eq) of a solution of diisobutyl aluminum hydride (1 M in hexane) is dropped slowly. After the addition, the solution is stirred for further 15 min at −78° C., before the reacting mixture is quenched by addition of 50 mL of water at the same temperature. With vigorous stirring, it is warmed up to RT and the cloudy solution is filtered over Celite. The filtrate is concentrated in dryness and the residual water is removed by codestillation with toluene. Light-colored oil is obtained and it is used without further purification in the subsequent reaction.

TLC control: petroleum ether/ethyl acetate 8:2, $R_f$=0.54

Yield: 13.3 g, >100% (purity 86.1%)

500-MHz-$^1$H-NMR-cosy ($DMSO_{d6}$): δ [ppm]=9.65 (s, 1H, H-4), 4.63 (dd, 1H, H-1, $J_{1/2a}$=4.8 Hz, $J_{1/2b}$=9.85 Hz), 2.51-2.50 (m, 1H, H-$3_a$), 2.48-4.40 (m, 1H, H-$3_b$), 2.27-2.20 (m, 1H, H-2a), 1.98-1.91 (m, 1H, H-$2_b$), 1.44 (s, 18H, 6*$CH_3$(Boc)), 1.92 (s, 9H, 3*$CH_3$(O-tBu)

ESI-MS: 410.4 $[M+Na]^+$ (S,E)-7-tert-Butyl 1-methyl 6-(bis(tert-butoxycarbonyl)amino)hept-2-enedioate

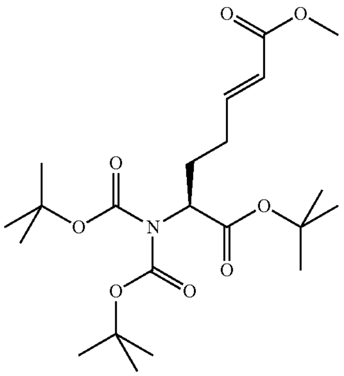

Molecular formula: C22H37NO8
Molecular weight: 443.53

13.2 g of $Boc_2$-Glu(H)-OtBu (~32.8 mmol) are provided in 20 mL of dried benzene and under argon atmosphere at RT a solution of 11.2 g of (methoxycarbonylmethylen)-triphenyl-phosphorane (32.8 mmol) is added. After stirring overnight, the solvent is removed in vacuo and the obtained oily residue is purified by chromatography on silica gel (column: 39*6.0 cm, petroleum ether/ethyl acetate 9:1).

Column chromatography: collected in 250 mL fractions, product: fractions 2-12

TLC control: petroleum ether/ethyl acetate 8:2, $R_f$=0.54

Yield: 12.0 g, 27.1 mmol, 83%

500-MHz-$^1$H-NMR-cosy ($DMSO_{d6}$): δ [ppm]=6.66 (dt, 1H, H-4, $J_{4/3}$=6.8 Hz $J_{4/5}$=15.9 Hz), 5.64 (d, 1H, H-5, $J_{5/4}$=15.9 Hz), 4.45-4.2 (m, 1H, H-1), 3.44 (s, 3H, $CH_3$-6), 2.01-1.95 (m, 2-H, H-$3_a$, H-$3_b$), 1.95-1.86 (m, 1H, H-$2_a$), 1.78-1.67 (m, 1H, H-$2_b$), 1.24 (s, 18H, 6*$CH_3$(Boc)), ESI-MS: 466.3 $[M+Na]^+$ (S,E)-2-(tert-Butoxycarbonylamino)-7-methoxy-7-oxohept-5-enoic acid (1a1)

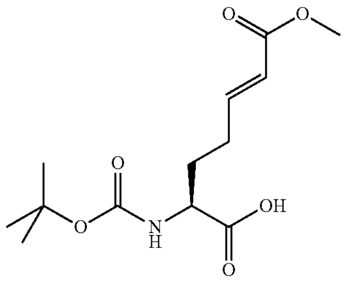

Molecular formula: C13H21NO6
Molecular weight: 287.31

7.0 g of (S,E)-7-tert-butyl 1-methyl 6-(bis(tert-butoxycarbonyl)amino)hept-2-enedioate (15.8 mmol) are dissolve in 40 mL of dichloromethane and added into the solution of 70 mL of trifluoroacetic acid. It is stirred at RT for 4 h. The solvent is removed in vacuo and the green residue is dried under high vacuum. The obtained oil is further used without purification. By successive addition of DIPEA the pH value is adjusted to ca. 7.

The oil is taken up in 50 mL of DMF and treated with 5.37 mL of DIPEA. 4.08 g of Boc-OSu (18.9 mmol, 1.2 eq) are added and stirred at RT overnight. The solvent is removed in vacuo and the residue is suspended in 130 mL of 5% $KHSO_4$ solution. It is extracted with ethyl acetate (1×150 mL, 2×100 mL) and the corrected organic phases are washed with brine (75 mL). After drying of the organic phase over $Na_2SO_4$ the solvent is removed in vacuo. The residue is purified by chromatography on silica gel (column: 13*6.0 cm, toluene/ethyl acetate 65:35, 0.5% acetic acid). Colorless oil is obtained.

Column chromatography: collected in 200 mL fractions, product: fractions 2-5, first running 500 mL TLC control: toluene/ethyl acetate 1:1, 0.5% acetic acid, $R_f$=0.35

Yield: 4.04 g, 14.1 mmol, 89% (purity 88.6%)

ESI-MS: 310.1 $[M+Na]^+$

Example 1.2 Preparation of pyridinone Derivatives

Benzyl-3-hydroxypyridin-3-yl-carbamate

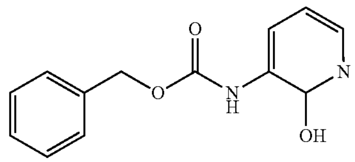

Molecular formula: C13H12N2O3
Molecular weight: 244.25

15 g of 2-hydroxy-nicotinic acid (108 mmol) are suspended in 180 mL of dried dioxane. After addition of 14.9 mL of triethylamine (108 mmol), the suspension is clear extensively. 24 mL of diphenyl phosphoryl azide (DPPA, 108 mmol) are added and the reaction solution is refluxed (130° C.) under argon atmosphere. Thereby, a gas emission is observed. After 16 h, further 16.3 mL of TEA and 12.8 mL of benzyl alcohol (117 mmol, 1.1 eq) are added successively and refluxed for further 24 h.

The solvent is removed in vacuo and the obtained brown residue is taken up in a mixture of 300 mL of DCM and 300 mL of brine. By 1M HCl solution the pH value is adjusted to ca. 1 (ca. 22 mL), the phases are separated and subsequently the water phase is extracted two times with each 200 mL of DCM. The corrected organic phases are washed with 10% $NaHCO_3$ solution (3×150 mL) and brine (1×150 mL), dried over $Na_2SO_4$, filtered and concentrated in vacuo in dryness. The obtained brown solid is recrystallized from 300 mL of methanol.

TLC control: DCM/MeOH 9:1, Rf=0.70

Yield: 16.2 g, 66.4 mmol, 62% (pale brown, felt-like solid)

ESI-MS: 245.1 $[M+H]^+$ tert-Butyl 2-(3-(benzyloxycarbonylamino)-2-oxopyridin-1(2H)-yl)acetate

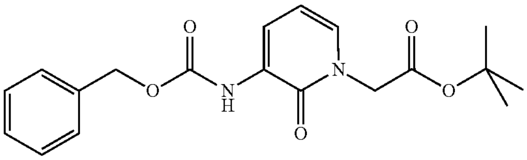

Molecular formula: C19H22N2O5
Molecular weight: 358.39

16.2 g of benzyl-3-hydroxypyridin-3-yl-carbamate (66.4 mmol) are suspended in 900 mL of absolute THF and cooled to 0° C. under argon atmosphere and 2.92 g of NaH (60% in mineral oil, 73.1 mmol, 1.1 eq) are added. To the resulting solution after the end of gas emission (ca. 15 min) 13.7 mL of bromoacetic acid tert-butylester (89.7 mmol, 1.35 eq) are added. It is stirred still for 15 minutes at 0° C. and subsequently at RT overnight. The reaction mixture is filtered and the filtrate is concentrated in dryness. The residue is taken up in 5 mL of ethyl acetate and treated with ca. 50 mL of diethylether and the resulting suspension is precipitated in the refrigerator overnight. The crystals are filtered off and washed with a little amount of ether.

The filtrate is concentrated and purified by chromatography on silica gel. (bed: 20×6 cm, eluent: petroleum ether/ethyl acetate=8/2)

Column chromatography: collected in 250 mL fractions, product: fractions 10-25

TLC control: petroleum ether/ethyl acetate=7/3, Rf=0.46

Yield: 19.3 g, 54.0 mmol, 81%

ESI-MS: 359.1 $[M+H]^+$ 2-(3-(Benzyloxycarbonylamino)-2-oxopyridin-1(2H)-yl)acetic acid

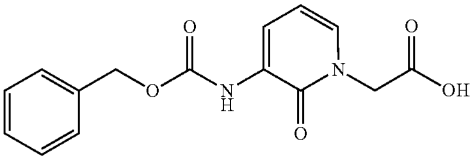

Molecular formula: C15H14N2O5
Molecular weight: 302.28

4.00 g of tert-butyl 2-(3-(benzyloxycarbonylamino)-2-oxopyridin-1(2H)-yl)acetate (11.2 mmol) are dissolved in 50 mL of dichloromethane and treated with 50 mL of trifloroacetic acid. It is stirred at RT for 3 h, before the volatile components are removed in vacuo. After drying under high vacuum a brown solid is obtained and it is suitable for the further use without purification.

Yield: 3.70 g, >100%

ESI-MS: 303.2 $[M+H]^+$

Benzyl-1-(2-(2-ethylbutylamino)-2-oxoethyl)-2-oxo-1,2-dihydro-pyridin-3-ylcarbamate

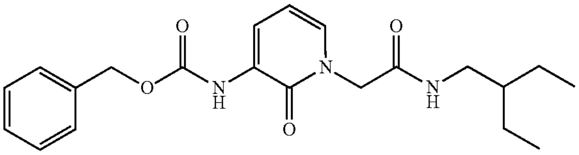

Molecular formula: C21H27N3O4
Molecular weight: 385.46

A mixture of 3.70 g of 2-(3-(benzyloxycarbonylamino)-2-oxopyridin-1(2H)-yl)acetic acid (~11.2 mmol), 3.58 g of TBTU (11.2 mmol), 1.51 g of HOBt (11.2 mmol) is dissolved in 60 mL of DMF. By addition of 5.70 mL of DIPEA (33.5 mmol, 3 eq) a pH value is adjusted to ~10. 1.50 mL of 2-ethyl-butylamine (11.2 mmol) is added and the mixture is stirred at RT overnight. The solvent is removed in vacuo and the obtained residue is taken up in 300 mL of DCM and subsequently washed with 10% citric acid (3×75 mL), saturated $NaHCO_3$ solution (3×75 mL) and brine (75 mL). The organic phase is dried over $Na_2SO_4$, filtered and concentrated in dryness. Pale brown solid is obtained and it is suitable for further processing without further purification.

Yield: 5.22 g, >100%

ESI-MS: 386.3 $[M+H]^+$ 2-(3-Amino-2-oxopyridin-1(2H)-yl)-N-(2-ethylbutyl)acetamide (2a)

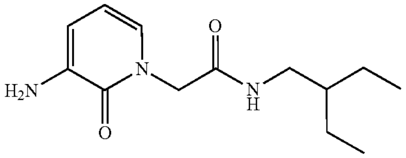

Molecular formula: C13H21N3O2
Molecular weight: 251.32

5.22 g of benzyl-1-(2-(2-ethylbutylamino)-2-oxoethyl)-2-oxo-1,2-dihydro-pyridin-3-ylcarbamate (2.4, ~11.2 mmol) are dissolved under nitrogen atmosphere in 60 mL of methanol. To this solution, 500 mg of Pd/C (10%) are added and stirred under hydrogen atmosphere at atmosphere pressure for 2.5 h. The catalysis is separated by filtration over silica gel, before the solvent is removed in vacuo. Dark oil is obtained and it is suitable for further processing without further purification.

Yield: 3.62 g, >100%

ESI-MS: 252.2 $[M+H]^+$

Example 1.3 Preparation of (S,E)-Methyl 6-(tert-butoxycarbonylamino)-7-(1-(2-(2-ethylbutylamino)-2-oxoethyl)-2-oxo-1,2-dihydro-pyridin-3-ylamino)-7-oxohept-2-enoate

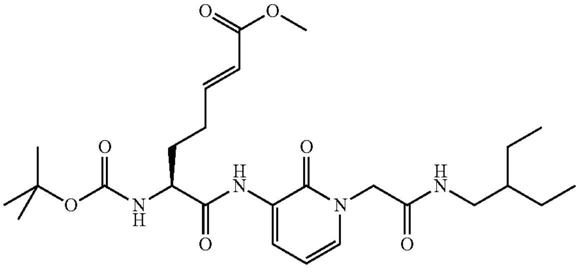

Molecular formula: C26H40N4O7
Molecular weight: 520.62

A solution of 3.36 g of 2-(3-amino-2-oxopyridin-1(2H)-yl)-N-(2-ethylbutyl)acetamide (2a, ~10.4 mmol) in 20 mL of DMF is provided. To this solution, a solution of 2.97 g of (S,E)-2-(tert-butoxycarbonylamino)-7-ethoxy-7-oxohept-5-enoic acid (1a1, 10.4 mmol), 3.93 g of HATU (10.4 mmol) and 3.52 mL of DIPEA (20.7 mmol, 2 eq) in 40 mL of DMF is added. By successive addition of DIPEA the pH value is adjusted to ca. 7. The reaction mixture is stirred at 40° C. for 2.5 hours, as well as at RT overnight, before the solvent is removed in vacuo. The obtained brown residue is taken up in 250 mL of ethyl acetate and subsequently washed with 10% citric acid (3×75 mL), saturated $NaHCO_3$ solution (3×75 mL) and brine (75 mL). The organic phase is dried over $Na_2SO_4$ and concentrated in vacuo in dryness. The residue is purified by chromatography on silica gel (bed: 13×6 cm, eluent: toluene/acetone=7/3).

Column chromatography: 150 mL first running, corrected in 40 mL fractions, product: fraction 6-15

TLC control: DCM/MeOH=97/3, Rf=0.40

Yield: 3.34 g, 6.42 mmol, 62%

ESI-MS: 543.4 $[M+Na]^+$ (S,E)-Methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (Compound of Formula (I))

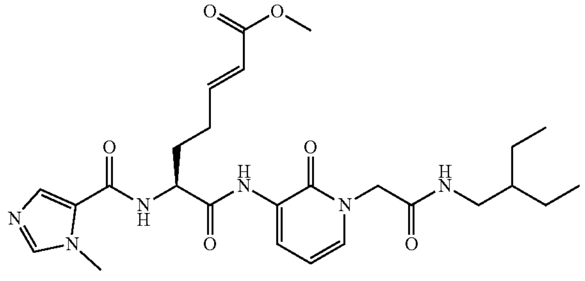

Molecular formula: C26H36N6O6
Molecular weight: 528.60

3.14 g of (S,E)-methyl 6-(tert-butoxycarbonylamino)-7-(1-(2-(2-ethylbutylamino)-2-oxoethyl)-2-oxo-1,2-dihydro-pyridin-3-ylamino)-7-oxohept-2-enoate (3.1, 6.03 mmol) are dissolved in a mixture of 25 mL of dichloromethane and 35 mL of TFA and stirred for 3 hours at RT, before the volatile components are removed in vacuo. The obtained brown oil is dried under high vacuum and dissolved in 10 mL of DMF and 1.03 mL of DIPEA (6.03 mmol) is added. To this a solution of 2.29 g of HATU (6.03 mmol) and 1.03 mL of DIPEA (6.03 mmol) in 30 mL of DMF is added. By successive addition of DIPEA the pH value is adjusted to ca. 7. It is stirred overnight at RT. The residue is taken up in 200 mL of ethyl acetate and subsequently washed with 10% citric acid, saturated $NaHCO_3$ solution and brine (each 75 mL). The organic phase is dried over $Na_2SO_4$, filtered and concentrated in vacuo in dryness. The residue is purified by chromatography on silica gel (bed: 12×6 cm, eluent: DCM/MeOH=97/3, after 2 Liters 95/5).

Column chromatography: 1000 mL first running, corrected in 50 mL fractions, product: fraction 43-66

TLC control: DCM/MeOH=97/3, $R_f$=0.30

Yield: 1.42 g, 2.69 mmol, 45%

ESI-MS: 551.3 $[M+Na]^+$ $^1$H-NMR (DMSO-d6, 500 MHz): δ [ppm]=9.29 (s, 1H), 8.63 (d, 1H), 8.21 (dd, 1H), 8.04 (t, 1H), 7.75 (d, 2H), 7.33 (dd, 1H), 6.93 (dt, 1H, J=15.63; 6.93), 6.25 (t, 1H), 5.86 (d, 1H, J=15.69), 4.58 (s, 2H), 3.79 (s, 3H), 3.62 (s, 3H), 3.01 (t, 2H), 2.33 (m, 2H), 2.03 (m, 1H), 1.90 (m, 1H), 1.26 (m, 5H), 0.83 (t, 6H)

Example 2 Preparation of the Hard Gelatine Capsule 2.1 Preparation A of the Hard Gelatine Capsule The preparation of the acidic granulate was performed by means of a wet granulation using 96% ethanol as a granulation liquid. Compound of formula (I), L-hydroxypropyl cellulose and sodium croscarmellose are sieved in the dry form, and mixed after that By adding ethanol, particle agglomeration and formation of the granulate structure results. Granulate mass is sieved in wet form, dried at 70° C., and finally sieved again. In a dry mixer, the sieved adipic acid as well as talc are added to the dry granulate and mixed. After that, the powder mixture is filled in a hard gelatine capsule.

2.2 Preparation B of the Hard Gelatine Capsule

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (15.0%) is mixed with polyvinylalkohol (56.9%). The mixture is treated in a hot melt extruder to obtain an extrudate. The extrudate is cooled, and milled. In a dry mixer, crospovidone (7.5%), L-hydroxypropyl cellulose (7.2%), fumaric acid (13.5%) are added to the milled extrudate and mixed. After that, the powder mixture is filled in a hard gelatine capsule.

2.3 Preparation C of the Hard Gelatine Capsule

Hydroxypropyl cellulose (2.3%) are dissolved in isopropanol (96%) to give the granulation liquid. (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (38.8%), cellulose (microcrystalline; 7.8%), polyvinyl caprolactam-polyvinyl acetate-polyethylene glycol graft co-polymer (7.8%), sodium croscarmellose (7.8%) and adipic acid (34.9%) are mixed. The granulation liquid is added to the powder blend whereby a granule mass is formed. The mass is sieved in a wet state, and then dried. After drying the mass is sieved again. Silicon dioxide (0.6%) is added to the drie granules in a dry mixer. Thereafter, the powder mixture is filled in a capsule.

Example 3

Pharmacokinetic of Compound of Formula (I) after Oral Administration of the Systemic Formulation in Human The pharmacokinetic of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound of formula (I)) was investigated in healthy volunteers. Cohorts of 18 subjects each were treated with an oral daily dose of 10, 20, 50 and 100 mg compound of formula (I), respectively over a time period of 7 days. The compound was administered in form of a systemic formulation manufactured according to the instructions described in example 2 (hard gelatine capsule).

The determination of said compound in blood plasma was performed by means of a previously validated HPLC-MS/MS method.

Figure 1:
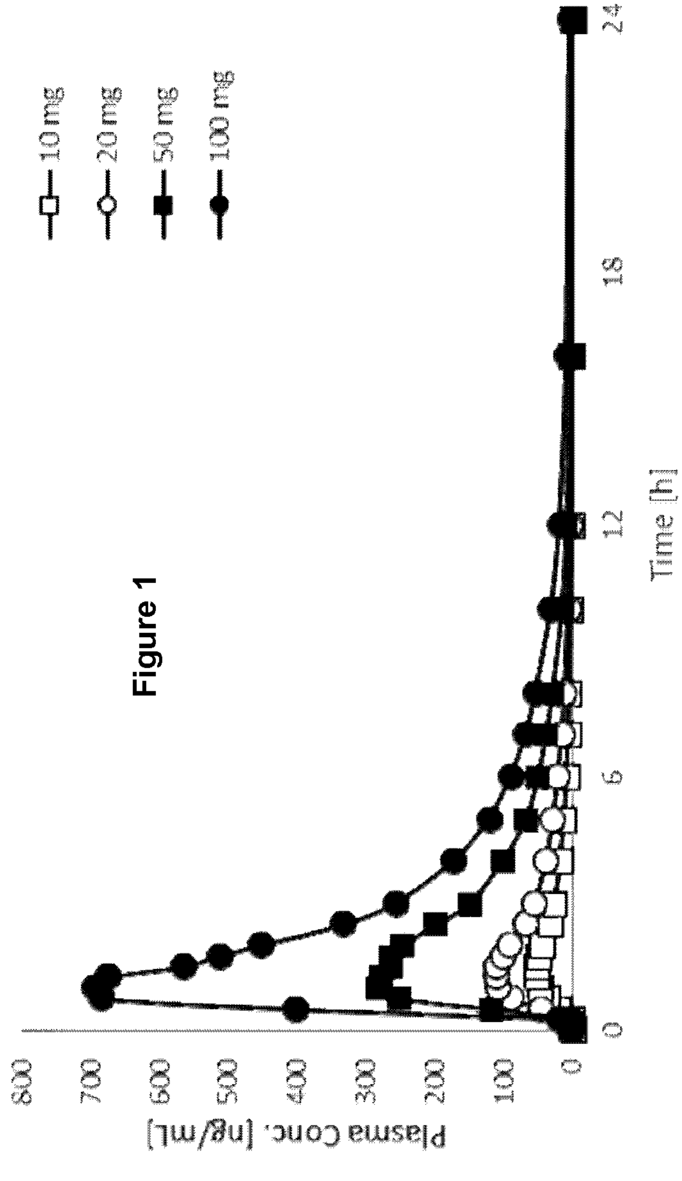
FIG. 1 shows the plasma profiles of the compound as well as the human pharmacokinetic data derivable thereof after the multiple dosing according to example 3.

Results: The plasma profiles of the compound as well as the human pharmacokinetic data derivable thereof after the multiple dosing are depicted in FIG. 1.

Conclusion: The plasma-profile exhibits a steep ascent of the drug level with a maximum at approximately 1 h after the administration. The relative early tmax of 1 h indicates an absorption in the upper small intestine, i.e. the duodenum and upper jejunum, which is the target site for treatment of celiac disease. Since the drug has to penetrate the intestinal mucosa during the absorption, it can be assumed that thereby a high local drug level is achieved temporally. In a first approximation, the maximal local concentration in the mucosa is assumed to be equivalent to the maximal plasma concentration. The drug concentration achieved with the formulation increases in the dose range 10-100 mg dose-proportionally, and when normalized to the body weight is remarkably higher than in the animal studies in which the drug was administered as a suspension.

Figure 2:
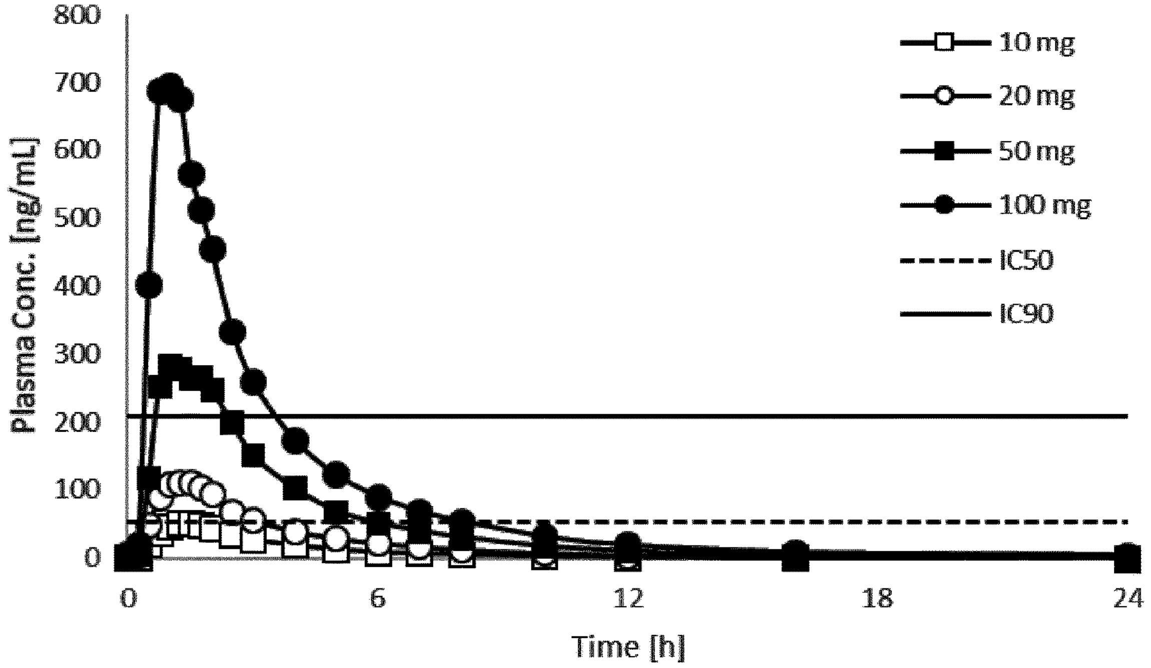
FIG. 2 shows the correlation of the human pharmacokinetic data with the in vitro data for the TG2 inhibition.

For the estimation of the therapeutic effective human dose, the drug concentration determined in vivo is compared with the drug concentrations resulting in an inhibition of the enzyme activity of TG2 in vitro (FIG. 2). Thereby, the TG2-mediated deamidation of gluten serves as a marker reaction. According to this correlation, the half maximal inhibition ($IC_{50}$) of TG2 is already achieved with a dose of 10 mg. A dose of 50 mg of the new developed formulation results in a drug level already exceeding the $IC_{90}$ of the enzyme inhibition. The 90% inhibition at $IC_{90}$ can be regarded as maximal pharmacodynamic effect.

Example 4 Comparison of Pharmacokinetic Data of the Formulation with Pharmacokinetic Data of the Plain Compound The human pharmacokinetic data of (5, E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound of formula (I)) described in example 3 were generated after administration of the hard gelatine capsule formulation described in example 2.

To estimate the influence of the formulation, the pharmacokinetic data of the hard gelatine formulation were compared with pharmacokinetic data generated after oral administration of the plain, unformulated compound. Due to regulatory and ethical reasons pharmacokinetic data with the plain compound were only generated in animals but not in human subjects.

The pharmacokinetic data of the plain compound were derived from several studies in monkeys, pigs, rabbits, rats and mice. In all studies the compound was administered orally after suspension in 0.5% (w/v) methylcellulose in water, pH 5±0.5. Blood samples were taken at various time points within 24 h after drug administration and quantified by means of a previously validated HPLC-MS/MS method.

Figure 3:
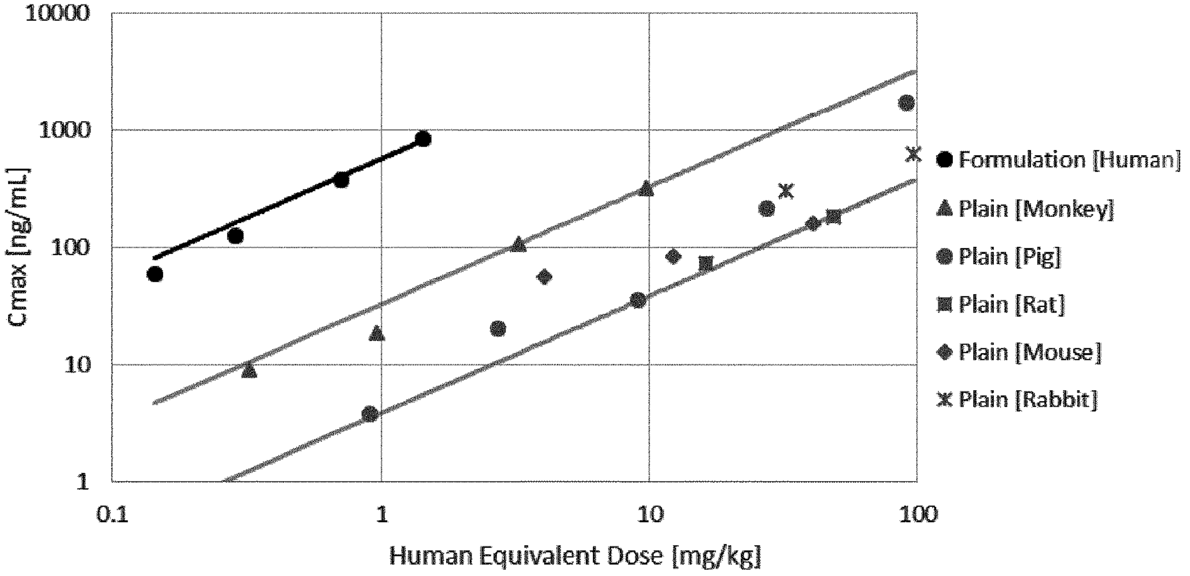
FIG. 3 shows the maximal plasma concentration (Cmax) reached after administration of different doses of compound of formula I in formulation or as a plain compound. In order to compile the data from different species, doses were converted into human-equivalent-dose (HED) taking into account differences in the body surface area between species. The widely accepted species-specific conversion factors defined in the FDA guideline "Estimating the Maximum Safe Starting Dose in Initial Clinical Trials for Therapeutics in Adult Healthy Volunteers" (Issue date 2005) were used.

FIG. 3 shows the maximal plasma concentration (Cmax) reached after administration of different doses of compound of formula I in formulation or as a plain compound. In order to compile the data from different species, doses were converted into human-equivalent-dose (HED) taking into account differences in the body surface area between species. The widely accepted species-specific conversion factors defined in the FDA guideline "Estimating the Maximum Safe Starting Dose in Initial Clinical Trials for Therapeutics in Adult Healthy Volunteers" (Issue date 2005) were used.

The comparison in FIG. 2 demonstrates over a wide dose range that the Cmax reached after administration of the formulation is more than 10-fold above the Cmax reached after administration of the plain compound. Although the differences in Cmax could partly be attributed to species differences in pharmacokinetics, the large difference between data from human and the closely related monkey suggest that the formulation plays a major role in achieving a high systemic exposure.

Example 5

The saturation solubility of compound of formula (I) was measured in the pH-range from 1 to 6.8 using HPLC/UV.

Figure 4:
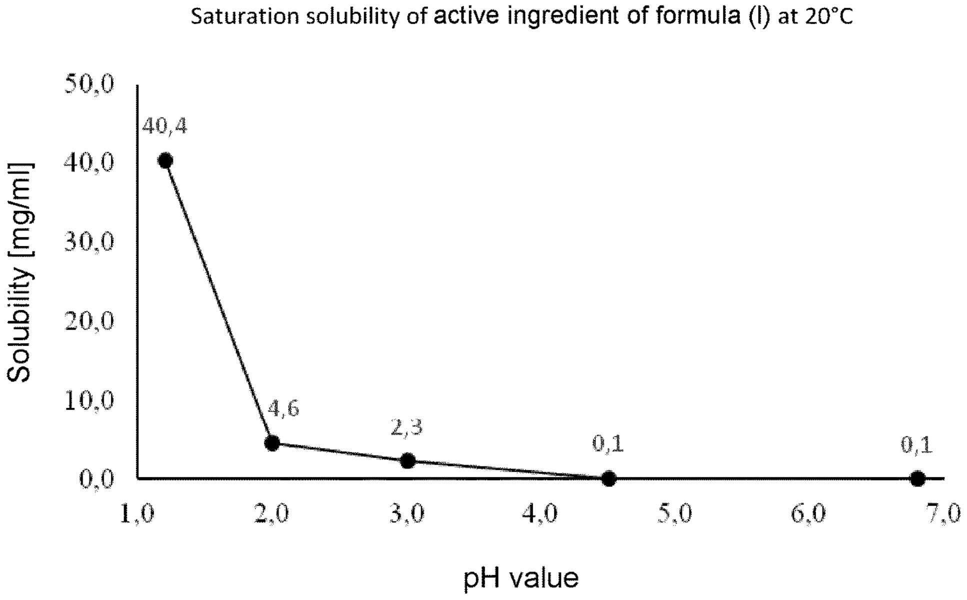
FIG. 4 shows the saturation solubility of (S,E)-methyl-7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate.

The results are illustrated in FIG. 4.

Results: It is apparent that the saturation solubility is much lower at a pH=6.8 (duodenum) than at a pH~1.

Example 6

Simulation of the Gastrointestinal-Tract—Transfer Model (Improvement of the Saturation Solubility)

The solubility of the dose as well as the dissolution velocity under physiological conditions are critical parameters for the oral availability at the target site. The investigation of the formulation in a transfer model enables the simulation of the in vivo conditions after the oral intake and thus the prediction how the drug take effect during the transfer from the stomach into the intestine.

When using bio-relevant media, additional information about the behaviour of the formulation under physiological conditions can be obtained with this model.

Experimental Arrangement

Figure 5:
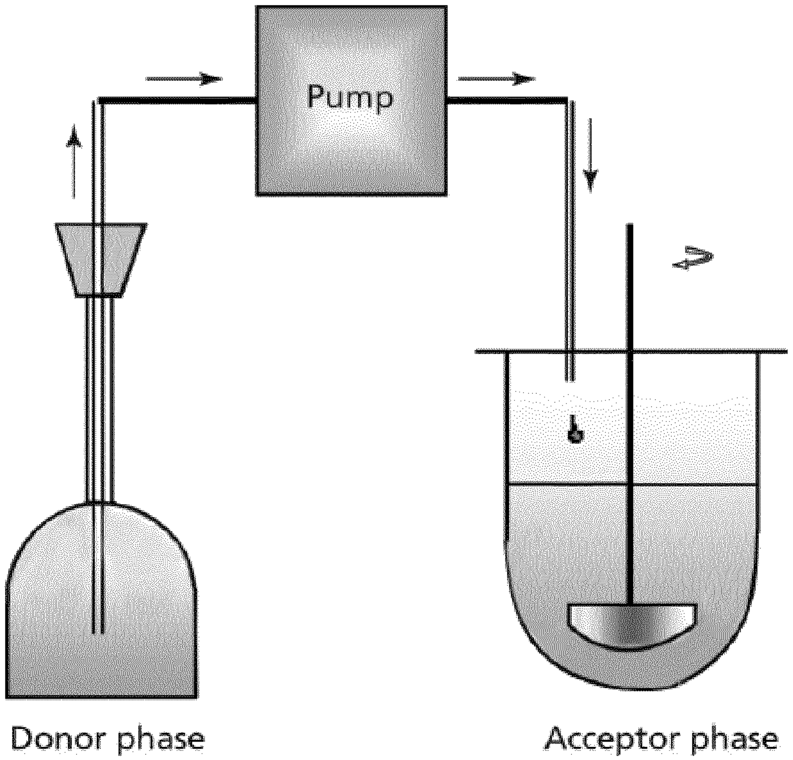
FIG. 5 shows a simulation of the gastrointestinal-tract—transfer model as an evidence of the high concentration of the drug in the duodenum.

The transfer model consists of a vessel with 125 ml donor medium and a vessel with 500 m acceptor medium. The donor medium is transferred by means of pump (Piston pump Sotax CP7) in the acceptor medium so that 625 ml liquid is present in the acceptor vessel at the end of the experiment. The transfer rate amounts 10 ml/min. The donor medium is an artificial gastric juice in a sober state, and contains 34.2 mM sodium chloride (NaCl) in 0.1 hydrogen chloride (HCl). The acceptor medium consists of artificial gastric juice in a sober state (FaSSIF) and contains 3 mM sodium taurocholate, and 0.75 nM lecithine in phosphate buffer with a pH-value of 6.5. The temperature of the acceptor medium is adjusted to 37.5° C.±0.5° C. For the simulation of the gastrointestine motility, the acceptor medium is stirred continuously with a stirring paddle (50 rpm). A calibrated stirring paddle apparatus 2 according to the conditions of the USP (Sotax AT7 Smart) as an acceptor vessel is used. In FIG. 5, a scheme of the apparatus is illustrated. The solubility of compound of the formula (I) is 4.4 mg/ml in the donor medium, and 0.2 mg/ml in the acceptor medium. Therefore, the weak basic drug moves from a medium with a pH-value being favourable for the solubility of the drug in a medium with a pH-value being unfavourable for the solubility of the drug.

Experimental Procedure

For the experiment a hard capsule of compound of formula (I) was used with the following composition, wherein a double determination was performed (n=2):

200 mg Compound of formula (I)
360 mg Adipic acid
40 mg L-hydroxypropyl cellulose
40 mg Sodium croscarmellose
20 mg Talc
94.08 mg Gelatine
1.92 mg Titanium dioxide The capsule was added to the donor medium. After the decomposition of the formulation, the transfer of the donor medium was started (transfer rate: 10 ml/min.) Over a time period of 120 min., probes were taken from the transfer medium, and the released and dissolved drug amount measured photometrically at 316 nm.

Figure 6:
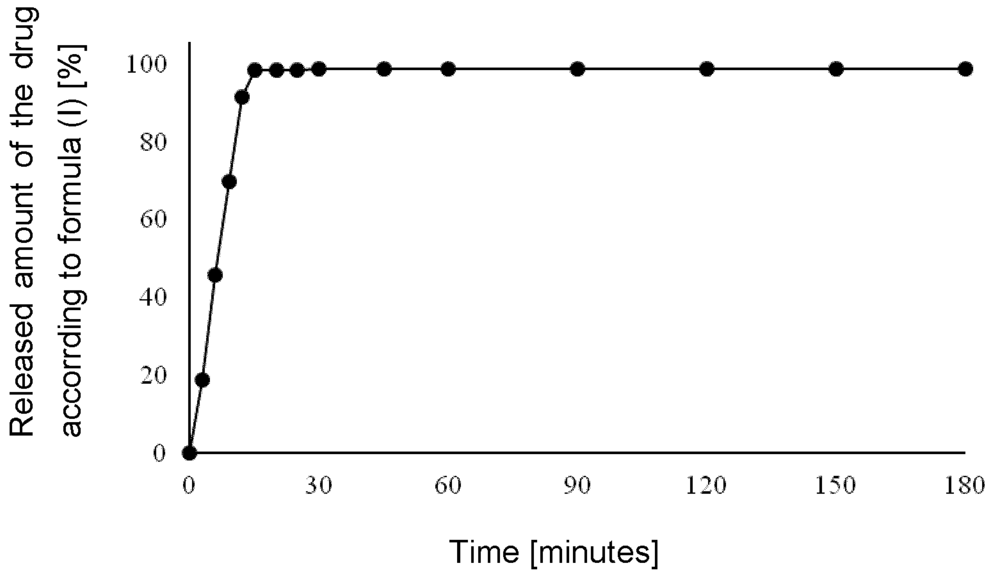
FIG. 6 shows the amount of the API which is released in the acceptor medium over the time in the transfer model.

The amount of the API which is released in the acceptor medium over the time is depicted in FIG. 6.

Results: The transfer of the artificial gastric juice was completed after 12.5 minutes. At the end of the transfer the pH-value of the acceptor medium was 6.4. The drug was completely dissolved in the donor medium and remained also completely dissolved in the acceptor medium over a period of 180 min. A precipitation was not observed. Thus, a solubility of 0.32 mg/ml (200 mg of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in 625 ml) for the tested dose of 200 mg was achieved. At a pH-value of 6.5 the saturation solubility of the pure drug is merely 0.18 mg/ml. Thus, an oversaturation factor of 1.8 was achieved, i.e. the concentration achieved in the FASSIF medium after the transfer lay remarkably above the saturation solubility of the drug in this medium.

Example 7: Preparation of a Pharmaceutical Composition in Form of a Tablet 7.1 Preparation A of a Pharmaceutical Composition in Form of a Tablet In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (7.6%) is mixed with L-hydroxypropyl methylcellulose (18.3%), croscarmellose sodium (1.5%), povidone K25 (8.4%) and cellulose (microcrystalline; 36.6%). The powder blend is granulated with ethanol (96%). After wet sieving the granules are dried. Adipic acid (13.7%), croscarmellose sodium (12.2%) and silicon dioxide (1.5%) are added to the granules to obtain the final blend which is compressed to tablets.

The tablet can then be coated with a film consisting of: lactose monohydrate, hydroxypropyl methylcellulose (E464; also known as hypromellose), titanium dioxide (E171), triacetin (E1518), iron oxide yellow (E172), and carnauba wax (E903).

7.2 Preparation B of a Pharmaceutical Composition in Form of a Tablet

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (22.0%) is mixed with L-hydroxypropyl methylcellulose (10.6%), croscarmellose sodium (11.0%), and mannitol (11.0%). The powder blend is granulated a solution of hydroxypropyl cellulose (1.3%) in ethanol (96%). After wet sieving the granules are dried. Glutaric acid (39.7%), and talcum (4.4%) are added to the granules to obtain the final blend which is compressed to tablets.

The tablet can then be coated with a film consisting of: hydroxypropyl methylcellulose, (E464; also known as hypromellose), titanium dioxide (E171), macrogol, iron oxide red (E172), and carnauba wax (E903).

7.3 Preparation C of a Pharmaceutical Composition in Form of a Tablet

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (15.4%) is mixed with polyvinylalkohol (58.6%). The mixture is treated in a hot melt extruder to obtain an extrudate. The product is cooled, milled, and mixed with croscarmellose sodium (6.2%), cellulose (microcrystalline; 6.2%), glutaric acid (12.4%), silicon dioxide (0.6%), and talc (0.6%) to obtain the final blend which is compressed to tablets.

The tablet can then be coated with a film consisting of: lactose monohydrate, hydroxypropyl methylcellulose (E464; also known as hypromellose), titanium dioxide (E171), triacetin (E1518), iron oxide yellow (E172), and carnauba wax (E903).

Example 8: Preparation of Granules for Capsules 8.1 Preparation A of Granules for Capsules 24 mg L-hydroxypropyl cellulose are dissolved in 22 ml ethanol to give the granulation liquid. 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 mg L-hydroxypropyl cellulose (low substituted, 25 mg sodium croscarmellose and 25 mg manitol are mixed. The granulation liquid is added to the powder blend whereby a granule mass is formed. The mass is sieved in a wet state, and then dried. After drying the mass is sieved again. 18 mg adipic acid and 5 mg talc are added to the drie granules in a dry mixer. Thereafter, the powder mixture is filled in a capsule.

8.2 Preparation a of Granules for Capsules

Hydroxypropyl cellulose (1.3%) are dissolved in ethanol (96%) to give the granulation liquid. (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (22.0%), L-hydroxypropyl cellulose (low substituted; 10.6%), sodium croscarmellose (11.0%) and manitol (11.0%) are mixed. The granulation liquid is added to the powder blend whereby a granule mass is formed. The mass is sieved in a wet state, and then dried. After drying the mass is sieved again. adipic acid (39.7%) and talc (4.4%) are added to the drie granules in a dry mixer. Thereafter, the powder mixture is filled in a capsule.

Example 9: Micronization Process

The (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate is micronized, wherein the particle size distribution is preferably defined by d(0.1) from 0.1 to 5 μm, d(0.5) from 0.3 to 10 μm, d(0.95) from 3 to 25 μm and the particle size range is from 0.1 to 100 μm.

Example 10

The efficacy and safety of a 6-week treatment with the compound of formula (I) in the hard gelatine capsule formulation described in example 2 was investigated in 160 adult patients with Celiac Disease (CeD). Patients, who were in clinical and histological remission at start of the study were challenged with 3 grams daily gluten intake and randomized to receive placebo or one of 3 doses of the compound of formula (I), i.e. 10 mg, 50 mg or 100 mg.

Each morning after at least 6 hours of fasting, patients took the study drug orally, followed by one biscuit containing 3 g of gluten 30 minutes later, before breakfast. Throughout the 6-week study, patients were required to continue their strict gluten free diet.

The primary endpoint of the study was, whether the compound of formula (I) could prevent gluten-induced change in intestinal mucosal morphology. Before start (baseline) and after end of the 6 weeks of treatment endoscopies were conducted by an experienced gastroenterologist. Four endoscopy forceps biopsy samples with one biopsy bite per pass were taken from the second and third part of the duodenum and preserved in a PAXgene fixative containers. Tissue slides of the biopsies were scanned as whole-slide images and the villous height (VH) and crypt depth (CrD) in the mucosal samples were measured. In addition, the density of CD3+ intra-epithelial lymphocytes (IELs), an indicator of inflammation, was counted. Symptoms of CeD the patients were recorded by patient-reported outcomes (PROs) and measured by the Celiac Symptom Index (CSI) (Ref1) and Celiac Disease Questionnaire (CDQ) (Ref2).

Figure 7:
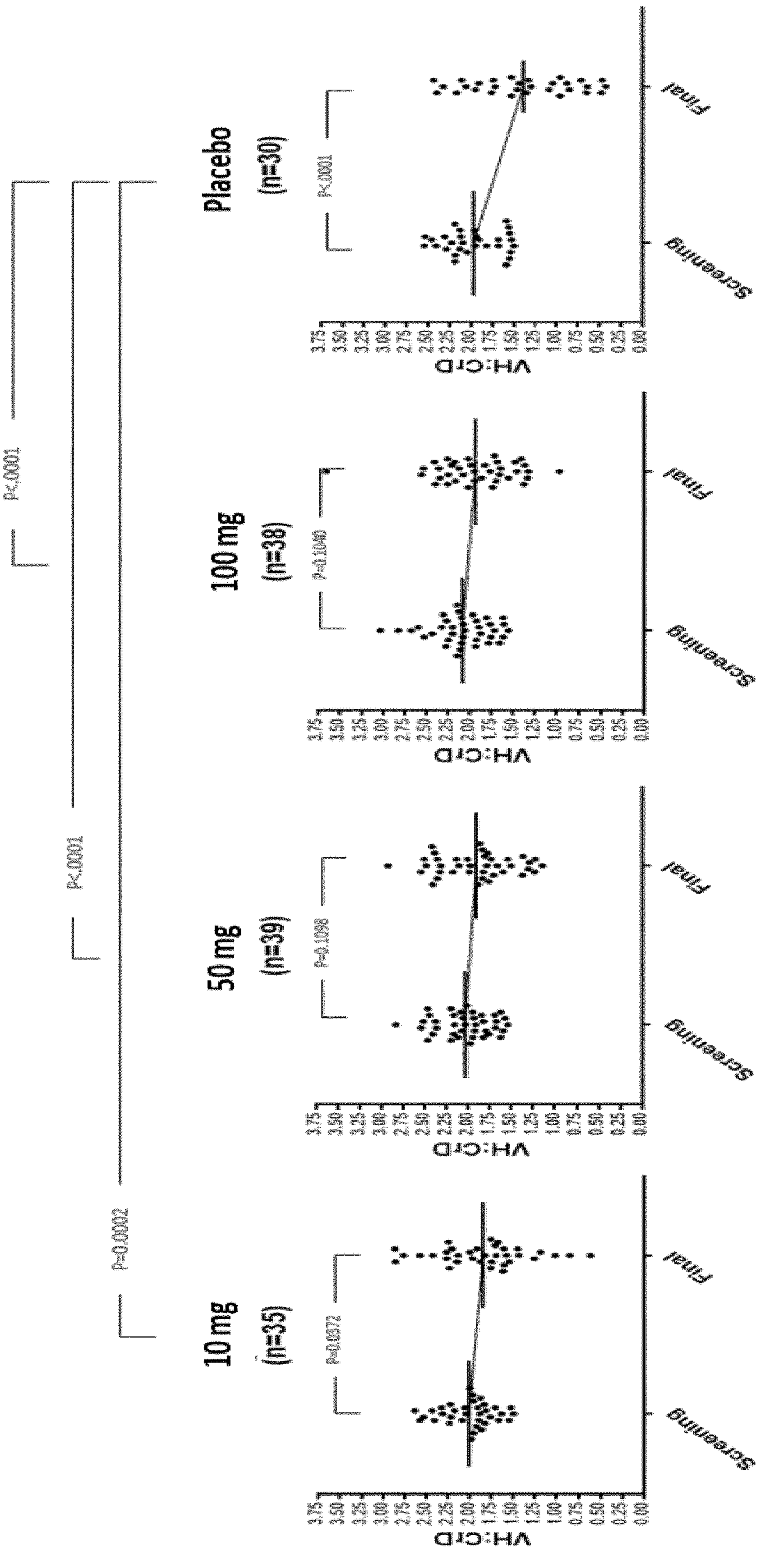
FIG. 7 shows individual patient's villus height-to-crypt depth ratio.

Histology-related efficacy endpoints could be evaluated in 142 patients who had sufficient biopsy samples at both baseline and week 6 (after gluten challenge and study treatment), including 35, 39, 38, and 30 patients in the 10 mg, 50 mg, 100 mg and placebo groups, respectively. The gluten challenge caused a significant deterioration in the mucosal morphology in the placebo group, as expected ($P<0.0001$). Daily doses of 50 mg and 100 mg the compound of formula (I) almost completely prevented the deleterious effect of gluten on VH:CrD, showing no significant reductions from baseline to week 6 ($P=0.1098$ and $P=0.1040$, respectively), while the 10 mg dose prevented mucosal deterioration to a lesser degree ($P=0.0372$). In comparison with placebo, all 3 doses of ZED1227 led to statistically significant differences in the VH:CrD change from baseline (P)≤0002 for all comparisons) (FIG. 7).

The ingested gluten caused an increase from baseline in IEL density, significantly in the placebo group and the 10 mg and 50 mg groups ($P<0.0001$) but not in the 100 mg group ($P=0.3757$). The difference between 100 mg ZED1227 and placebo in the change in IEL density was statistically significant ($P=0.0001$). (FIG. 8)

The CSI score, indicating worsening CeD-related symptoms, increased from baseline to week 6, during gluten challenge, and then returned to baseline at the follow-up visit. The comparison with placebo was significant in favor of the 10 mg and 100 mg doses of ZED1227 ($P<0.05$) but not the 50 mg dose (FIG. 9).

Despite the gluten challenge, the CDQ scores increased, which indicated better quality of life, from baseline to week 6 in the 10 mg, 50 mg, and 100 mg groups, while the CDQ total score decreased in the placebo group. The difference was significant for the 10 mg and 100 mg doses compared with placebo ($P<0.05$ for both) (FIG. 10A). Similarly, the changes in the CDQ gastrointestinal subscore from baseline to week 6 favored ZED1227, reaching significance for the 10 mg and 100 mg doses compared with placebo ($P<0.05$ for both) (FIG. 10B).

The safety profile, i.e. the frequency and severity of adverse events, of the compound of formula (I) in the hard gelatine capsule formulation described in example 2 was comparable to placebo.

In conclusion, the compound of formula (I) in the hard gelatine capsule formulation described in example 2 effectively prevented intestinal mucosal injury in patients with celiac disease challenged with a moderate dose of daily gluten. In addition gluten-induced symptoms and quality of life were significantly improved.

REFERENCES

Ref. 1 Leffler D A, Dennis M, Edwards George J, et al. A validated disease-specific symptom index for adults with celiac disease. Clinical gastroenterology and hepatology: the official clinical practice journal of the American Gastroenterological Association 2009; 7:1328-34.

Ref. 2Häuser W, Gold J, Stallmach A, Caspary W F, Stein J. Development and validation of the Celiac Disease Questionnaire (CDQ), a disease-specific health-related quality of life measure for adult patients with celiac disease. Journal of clinical gastroenterology 2007; 41:157-66.

The invention claimed is:

1. A method for the prophylaxis or treatment of coeliac disease in a subject, comprising:

administering to the subject a systemic formulation comprising an effective amount of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

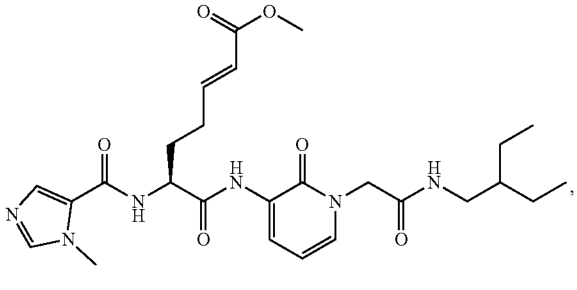

, or an enantiomer, a solvate, a hydrate or a pharmaceutically acceptable salt thereof, and at least one acidifier, wherein the mass ratio of the at least one acidifier relative to (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 15 to 0.1 m/m.

2. The method according to claim 1, wherein the systemic formulation is an oral formulation.

3. The method according to claim 1, wherein the systemic formulation further comprises at least one binder, at least one polymeric precipitation inhibitor, or a combination of at least one binder and at least one polymeric precipitation inhibitor.

4. The method according to claim 1, wherein the acidifier is selected from the group consisting of ascorbic acid, organic di-carboxylic acids.

5. The method according to claim 3, wherein the at least one binder is selected from the group consisting of sugar, sucrose, polysaccharides, xanthan gum, guar gum, carrageenan, starches derived from wheat, corn, rice, or potatoes, preagglutinated (modified) starch derived from wheat, corn, rice, or potatoes, sodium starch glycolate, natural gums, acacia gum, gelatin, tragacanth, derivatives of sea weed, alginic acid, sodium alginate, ammonium calcium alginate, cellulose, cellulose derivatives, and polyvinylpyrrolidone.

6. The method according to claim 3, wherein the acidifier is adipic acid and the at least one polymeric precipitation inhibitor is selected from the group consisting of polyvinyl alcohol, polyvinyl-caprolactam-polyvinyl acetate-polyethylene glycol graft copolymer, L-hydroxypropyl cellulose, hydroxypropyl cellulose and a combination of L-hydroxypropyl cellulose and hydroxypropyl cellulose.

7. The method according to claim 1, wherein the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxo-hept-2-enoate is in the form of particles having a particle size distribution which is defined by d (0.95)≤25 μm.

8. The method according to claim 1, wherein the systemic formulation comprises 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 1 wt % to 75 wt % acidifier, and wherein the systemic formulation further comprises 0.1 wt % to 40 wt % polymeric precipitation inhibitor, 0 wt % to 30 wt % binder, 0.1 wt % to 35 wt % disintegrant, and 0.1 wt % to 10 wt % lubricant/glidant.

9. The method according to claim 1, wherein the systemic formulation comprises 4.5 wt % to 55 wt % adipic acid.

10. The method according to claim 8, wherein the polymeric precipitation inhibitor is selected from the group consisting of polyvinyl alcohol, polyvinyl caprolactam-polyvinyl acetate-polyethylene glycol graft copolymer, L-hydroxypropyl cellulose, hydroxypropyl cellulose and a combination of L-hydroxypropyl cellulose and hydroxypropyl cellulose.

11. The method according to claim 9, wherein the systemic formulation further comprises 3.5 wt % to 30.5 wt % L-hydroxypropyl cellulose, 3.5 wt % to 30.5 wt % hydroxypropyl cellulose, or 3.5 wt % to 30.5 wt % of a combination of L-hydroxypropyl cellulose and hydroxypropyl cellulose.

12. The method according to claim 3, wherein the systemic formulation comprises 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 4.5 wt % to 55 wt % adipic acid, 3.5 wt % to 30 wt % L-hydroxypropyl cellulose, 0 wt % to 30 wt % mannitol, 2 wt % to 35 wt % sodium croscarmellose, and 1 wt % to 9 wt % talc or silicon dioxide.

13. The method according to claim 1, wherein the systemic formulation is in the form of a tablet, coated tablet, capsule, powder, or granules.

14. The method according to claim 13, wherein the systemic formulation is a capsule comprising 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 4.5 wt % to 55 wt % adipic acid, 3.5 wt % to 30 wt % L-hydroxypropyl cellulose, 2 wt % to 35 wt % sodium croscarmellose, and 1 wt % to 9 wt % talc.

15. The method according to claim 13, wherein the systemic formulation is a tablet comprising 0.1 wt % to 30 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 35 to 50 wt % microcrystalline cellulose, 5 wt % to 50 wt % adipic acid, 3.5 wt % to 30 wt % L-hydroxypropyl cellulose, 0.01 wt % to 30 wt % mannitol, 3.7 wt % to 15 wt % sodium croscarmellose, and 0.5 wt % to 4.00 wt % silicon dioxide.

16. The method according to claim 2, wherein the oral formulation is an oral solid formulation.

17. The method according to claim 1, wherein the mass ratio of the at least one acidifier relative to (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 11.5 to 1.8 m/m.

18. The method according to claim 1, wherein the mass ratio of the at least one acidifier relative to (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 2 to 1 m/m.

19. The method according to claim 1, wherein the systemic formulation is an oral dosage form containing 10 mg of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, or an enantiomer, a solvate, a hydrate or a pharmaceutically acceptable salt thereof.

20. The method according to claim 1, wherein the systemic formulation is an oral dosage form containing 20 mg of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, or an enantiomer, a solvate, a hydrate or a pharmaceutically acceptable salt thereof.

21. The method according to claim 1, wherein the systemic formulation is an oral dosage form containing 50 mg of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, or an enantiomer, a solvate, a hydrate or a pharmaceutically acceptable salt thereof.

22. The method according to claim 1, wherein the systemic formulation is an oral dosage form containing 100 mg of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, or an enantiomer, a solvate, a hydrate or a pharmaceutically acceptable salt thereof.

23. The method according to claim 1, wherein the systemic formulation is administered to the subject once daily.

24. The method according to claim 1, wherein the acidifier is ascorbic acid, oxalic acid, malonic acid, succinic acid, glutaric acid, tartaric acid, fumaric acid, maleic acid, malic acid, adipic acid, glutamic acid, citric acid, or sodium hydrogen citrate.

* * * * *